(12) United States Patent
Warzecha

(10) Patent No.: US 7,160,725 B2
(45) Date of Patent: Jan. 9, 2007

(54) HEDGEHOG SIGNALING PROMOTES THE FORMATION OF THREE DIMENSIONAL CARTILAGE MATRICES

(75) Inventor: Joerg Warzecha, Frankfurt (DE)

(73) Assignee: Curis, Inc., Cambridge, MA (US)

( * ) Notice: Subject to any disclaimer, the term of this patent is extended or adjusted under 35 U.S.C. 154(b) by 264 days.

(21) Appl. No.: 10/294,036

(22) Filed: Nov. 13, 2002

(65) Prior Publication Data

US 2003/0220244 A1 Nov. 27, 2003

Related U.S. Application Data

(60) Provisional application No. 60/350,594, filed on Nov. 13, 2001.

(51) Int. Cl.
*G01N 33/567* (2006.01)
*C12N 5/06* (2006.01)
*C07K 14/475* (2006.01)
*C07K 14/52* (2006.01)

(52) U.S. Cl. ............... 435/377; 435/7.21; 435/325; 530/399

(58) Field of Classification Search .............. 435/375; 514/12
See application file for complete search history.

(56) References Cited

U.S. PATENT DOCUMENTS

| 4,642,120 | A | | 2/1987 | Nevo et al. |
| 4,846,835 | A | | 7/1989 | Grande |
| 4,904,259 | A | | 2/1990 | Itay |
| 5,041,138 | A | | 8/1991 | Vacanti et al. |
| 5,053,050 | A | | 10/1991 | Itay |
| 5,206,023 | A | | 4/1993 | Hunziker |
| 5,270,300 | A | | 12/1993 | Hunziker |
| 5,486,359 | A | * | 1/1996 | Caplan et al. ............ 424/93.7 |
| 5,844,079 | A | | 12/1998 | Ingham et al. |
| 6,281,332 | B1 | | 8/2001 | Beachy et al. |

FOREIGN PATENT DOCUMENTS

| WO | WO 88/00205 | 1/1988 |
| WO | WO 89/09787 | 10/1989 |
| WO | WO 89/09788 | 10/1989 |

OTHER PUBLICATIONS

Wells (Sep. 18, 1990) Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) Genome Research 10:398.*
Skolnick and Fetrow (2000) Trends in Biotech. 18(1): 34.*
Doerks et al. (Jun. 1998) Trends in Genetics 14(6): 248.*
Smith and Zhang (Nov. 1997) Nature Biotechnology 15:1222.*
Brenner (Apr. 1999) Trends in Genetics 15(4): 132.*
Bork and Bairoch (Oct. 1996) Trends in Genetics 12(10): 425.*
Heng et al, 2004. Stem Cells. 22:1152-1167.*
Phillips, A., J Pharm Pharmacology 53: 1169-1174, 2001.*
Enomoto-Iwamoto, et al, 2000. Journal of Bone and Mineral Research. 15: 9 1659.*
Pettit et al. 1998. Trends Biotechnol. 16: 343-349.*
Pepinsky et al. J Biol Chem. May 29, 1998;273(22):14037-45.*
Aston, J.E. and Bentley, G. Repair of Articular Surfaces by Allografts of Articular and Growth-Plate Cartilage. J. Bone Joint Surg. 68B, 29-35 (1986).
Bentley, G. and Greer, R.B. Homotransplantation of Isolated Epiphyseal and Articular Cartilage Chondrocytes into Joint Surfaces of Rabbits. Nature 230, 385-388 (1971).
Bitgood, M.J. and McMahon, A.P. et al. Hedgehog and Bmp Genes Are Coexpressed at Many Diverse Sites of Cell-Cell Interaction in the Mouse Embryo. Dev. Biol. 172, 126-138 (1995).
Bumcrot, D.A. et al. Proteolytic Processing Yields Two Secreted Forms of Sonic hedgehog. Mol. Cell. Biol. 15, 2294-2303 (Apr. 1995).
Chang, D.T. et al. Products, genetic linkage and limb patterning activity of a murine hedgehog gene. Development 120, 3339-3353 (1994).
Davidson, E.H. How embryos work: a comparative view of diverse modes of cell fate specification. Development 108, 365-389 (1990).
Echelard, Y. et al. Sonic Hedgehog, a Member of a Family of Putative Signaling Molecules, is Implicated in the Regulation of CNS Polarity. Cell 75, 1417-1430 (1993).
Ekker, S.C. et al. Patterning activities of vertebrate hedgehog proteins in the developing eye and brain. Curr. Biol. 5, 944-955 (1995).
Ekker, S.C. et al. Distinct expression and shared activities of members of the hedgehog gene family of *Xenopus laevis*. Development 121, 2337-2347 (1995).
Ericson, J. et al. Sonic Hedgehog induces the Differentiation of Ventral Forebrain Neurons: A Common Signal for Ventral Patterning within the Neural Tube. Cell 81, 747-756 (1995).
Fan, C.-M. et al. Patterning of Mammalian Somites by Surface Ectoderm and Notochord: Evidence for Sclerotome Induction by a Hedgehog Homolog. Cell 79, 1175-1186 (1994).

(Continued)

Primary Examiner—Janet L. Andres
Assistant Examiner—Zachary C. Howard
(74) Attorney, Agent, or Firm—Fish & Neave IP Group, Ropes & Gray LLP

(57) ABSTRACT

The present invention provides methods and compositions for promoting the formation of three dimensional cartilage matrices. The present invention further provides methods of treating diseases and injuries involving cartilage and bone using the three dimensional cartilage matrices provided herein.

24 Claims, 8 Drawing Sheets

OTHER PUBLICATIONS

Fan, C.-M. et al. Long-Range Sclerotome Induction by Sonic Hedgehog: Direct Role of the Amino-Terminal Cleavage Product and Modulation by the Cyclic AMP Signaling Pathway. Cell 81, 457-465 (1995).

Fietz, M.J. et al. Secretion of the amino-terminal fragment of the Hedgehog protein is necessary and sufficient for hedgehog signaling in Drosophila. Curr. Biol. 5, 643-651 (1995).

Forbes, A.J. et al. hedgehog is required for the proliferation and specification of ovarian somatic cells prior to egg chamber formation in Drosophila. Development 122, 1125-1135 (1996).

Francis, P.H. et al. Bone morphogenetic proteins and a signaling pathway that controls patterning in the developing chick limb. Development 120, 209-218 (1994).

Freed, L.E. et al. Neocartilage formation in vitro and in vivo using cells cultured on synthetic biodegradable polymers. J. Biomed. Mater. Res. 27, 11 (1993).

Goodrich, L.V. et al. Conservation of the hedgehog/patched signaling pathway from flies to mice: induction of a mouse patched gene by Hedgehog. Genes Dev. 10, 301-312 (1996).

Grande, D.A. et al. The Repair of Experimentally Produced Defects in Rabbit Articular Cartilage by Autologous Chondrocyte Transplantation. J. Orthop. Res. 7, 208-218 (1989).

Green, W.T. Articular Cartilage Repair: Behavior of Rabbit Chondocytes During Tissue Culture and Subsequent Allografting. Clin. Orthop. 124, 237-250 (1977).

Gurdon, J.B. The Generation of Diversity and Pattern in Animal Development. Cell 68, 185-199 (1992).

Hahn, H. et al. Mutations of the Human Homolog of Drosphila patched in the Nevoid Basal Cell Carcinoma Syndrome. Cell 85, 841-851 (Jun. 14, 1996).

Hammerschmidt, M. et al. Protein kinase A is a common negative regulator of Hedgehog signaling in the vertebrate embryo. Genes Dev. 10, 647-658 (1996).

Honig, L.S. Positional signal transmission in the developing chick limb. Nature 291, 72-73 (1981).

Hooper, J.E. et al. The Drosophila patched Gene Encodes a Putative Membrane Protein Required for Segmental Patterning. Cell 59, 751 (1989).

Hynes, M. et al. Induction of Midbrain Dopaminergic Neurons by Sonic Hedgehog. Neuron 15, 35-44 (1995).

Ishizaki, Y. et al. Autocrine Signals Enable Chondrocytes to Survive in Culture. J. Cell Biol. 126, 1069-1077 (1994).

Jessell, T.M. et al. Diffusible Factors in Vertebrate Embryonic Induction. Cell 68, 257-270 (1992).

Johnson, R.L. et al. Ectopio Expression of Sonic hedgehog Alters Dorsal-Ventral Patterning of Somites. Cell 79, 1165-1173 (1994).

Johnson, R.L. et al. Human Homolog of patched, a Candidate Gene for the Basal Cell Nevus Syndrome. Science 272, 1668 (1996).

Krauss, S. et al. A Functionally Conserved Homolog of the Drosophila Segment Polarity Gene hh is Expressed in Tissues with Polarizing Activity in Zebrafish Embryos. Cell 75, 1431-1444 (1993).

Lai, C.-J. et al. Patterning of the neural ectoderm of *Xenopus laevis* by the amino-terminal product of hedgehog autoproteolytic cleavage. Development 121, 2349-2360 (1995).

Langer, F. and Gross, A.E. Immunogenicity of Allograft Articular Cartilage. J. Bone Joint Surg. 56A, 297-304 (1974).

Lee, J.J. et al. Secretion and Localized Transcription Suggest a Role in Positional Signaling for Products of the Segmentation Gene hedgehog. Cell 71, 33-50 (1992).

Lee, J.J. et al. Autoproteolysis in hedgehog Protein Biogenesis. Science 266, 1528-1537 (1994).

Levin, M. et al. A Molecular Pathway Determining Left-Right Asymmetry in Chick Embryogenesis. Cell 82, 803-814 (1995).

Lopez-Martinez, A. et al. Limb-patterning activity and restricted posterior localization of the amino-terminal product of Sonic hedgehog cleavage. Curr. Biol. 5, 791-795 (1995).

Marti, E. et al. Distribution of Sonic hedgehog peptides in the developing chick and mouse embryo. Development 121, 2537-2547 (1995).

Marti, E. et al. Requirement of 19K form of Sonic hedgehog for induction of distinct ventral cell types in CNS explants. Nature 375, 322-325 (1995).

Massaque, J. et al. The Transforming Growth Factor-Beta Family. Ann. Rev. Cell Biol. 6, 597-641 (1990).

Messner, K. Hydroxylapatite Supported Dacron Plugs for Repair of Isolated Full-Thickness Defects of the Rabbit Femoral Condyle. 40th Annual Meeting Orth. Res. Soc., New Orleans p. 239 (1994).

Munsterberg, A.E. et al. Combinatorial signaling by Sonic hedgehog and Wnt family members induces myogenic bHLH gene expression in the somite. Genes Dev. 9, 2911-2922 (1995).

Nakano, Y. et al. A protein with several possible membrane-spanning domains encoded by the Drosophila segment polarity gene patched. Nature 341, 508 (1989).

Nishimoto. Medulloblastoma. Med. J. Kinki University 15, 75-86 (1990).

Niswander, L. et al. A positive feedback loop coordinates growth and patterning in the vertebrate limb. Nature 371, 609-612 (1994).

Nixon, A.J. et al. Temporal matrix synthesis and histologic features of a chondrocyte-laden porous collagen cartilage analogue. Am. J. Vet. Res. 54, 349-356 (1993).

Nusslein-Volhard, C. and Wieschaus, E. Mutations affecting segment number and polarity in Drosophila. Nature 287, 795-801 (1980).

Pathi, S. et al. Comparative biological responses to human Sonic, Indian, and Desert hedgehog. Mechanisms of Development. 106, 107-117 (2001).

Perrimon, N. Cell 80, 517 (1995).

Perrimon, N. Serpentine Proteins Slither into the Wingless and Hedgehog Fields. Cell 86, 513 (1996).

Placzek, M. et al. Induction of floor plate differentiation by contact-dependent, homeogeneetic signals. Development 117, 205-218 (1993).

Porter, J.A. et al. The product of hedgehog autoproteolytic cleavage active in local and long-range signaling. Nature 374, 363-366 (1995).

Porter, J.A. et al. Hedgehog Patterning Activity: Role of a Lipophilic Modification Mediated by the Carboxy-Terminal Autopressing Domain. Cell 86, 21-34 (1996).

Rich, D. et al. The Use of Periosteal Cell/Polymer Tissue Constructs for the Repair of Articular Cartilage Defects. 40th Annual Meeting Orth. Res. Soc., New Orleans p. 241 (1994).

Riddle, R.D. et al. Sonic hedgehog Mediates the Polarizing Activity of the ZPA. Cell 75, 1401-1416 (1993).

Roberts, D.J. et al. Sonic hedgehog is an endodermal signal inducing Bmp-4 and Hox genes during induction and regionalization of the chick hindgut. Development 121, 3163-3174 (1995).

Robinson, D. et al. Regenerating Hyaline Cartilage in Articular Defects of Old Chickens Using Implants of Embryonal Chick Chondrocytes Embedded in a New Natural Delivery Substance. Calcif. Tissue Int. 46, 246-253 (1990).

Roelink, H. et al. Floor Plate and Motor Neuron Induction by vhh-1, a Vertebrate Homolog of hedgehog Expressed by the Notochord. Cell 76, 761-775 (1994).

Roelink, H. et al. Floor Plate and Motor Neuron Induction by Different Concentrations of the Amino-Terminal Cleavage Product of Sonic Hedgehog Autoproteolysis. Cell 81, 445-455 (1995).

Ruiz i Altaba, A. et al. Restrictions to Floor Plate Induction by hedgehog and Winged-Helix Genes in the Neural Tube of Frog Embryos. Mol. Cell. Neurosci. 6, 106-121 (1995).

Sporn, M.B. and Roberts, A.B. Transforming Growth Factor-Beta: Recent Progress and New Challenges. J. Cell Biol. 119, 1017-1021 (1992).

Stone, K.R. et al. Future Directions: Collagen-Based Prostheses for Meniscal Regeneration Clin. Orthop. Relat. Red. 252, 129-135 (1990).

Tabata, T. et al. The Drosophila hedgehog gene is expressed specifically in posterior compartment cells and is a target of engrailed regulation. Genes Dev. 6, 2635-2645 (1992).

Takigawa, M. et al. Chondrocytes dedifferentiated by serial monolayer culture from cartilage nodules in nude mice. Bone Miner. 2, 449 (1987).

Tanabe, Y. et al. Induction of motor neurons by Sonic hedgehog is independent of floor plate differentiation. Curr. Biol. 5, 651-658 (1995).

Vacanti, C.A. et al. Synthetic Polymers Seeded with Chondrocytes Provide a Template for New Cartilage Formation. Plast. Reconstr. Surg. 88, 753 (1991).

von Schroeder, H.P. et al. The use of polylactic acid matrix and periosteal grafts for the reconstruction of rabbit knee articular defects. J. Biomed. Mater. Res. 25, 329-339 (1991).

Wakitani, S. et al. Repair of Rabbit Articular Surfaces with Allograft Chondrocytes Embedded in Collagen Gel. J. Bone Joint Surg. 71B, 74-80 (1989).

Wang, M.Z. et al. Induction of dopaminergie neuron phenotype in the midbrain by Sonic hedgehog protein. Nature Med. 1, 1184-1188 (1995).

Weinberg, E.S. et al. Development regulation of zebrafish MyoD in wild-type, no tail and spadetail embryos. Development 122, 271-280 (1996).

Wozney. Bone Morphogenetic Proteins. Prog. Growth Fact. Res. 1, 267-280 (1989).

Yamada, T. et al. Control of Cell Pattern in the Neural Tube: Motor Neuron Induction by Diffusible Factors from Notochord and Floor Plate. Cell 73, 673-686 (1993).

Yoshinao, M. Immune Responses to Articular Cartilage Reconstruction using Chondrocytes Allograft Transplant. J. Jpn. Orth. Assoc. 64, 835-846 (1990).

* cited by examiner

| ANTIBODY | EXPRESSION |
|---|---|
| VIMENTIN | ++ |
| COLLAGEN II | ++ |
| INDIAN HEDGEHOG | - |
| PTHrp | + |
| BMPR-IA | - |
| BMPR-IB | + |
| BMPR-II | + |

Fig. 6

HEDGEHOG SIGNALING PROMOTES THE FORMATION OF THREE DIMENSIONAL CARTILAGE MATRICES

RELATED APPLICATIONS

This application claims priority to U.S. provisional application No. 60/350,594 filed Nov. 13, 2001, the disclosure of which is hereby incorporated by reference in its entirety.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365–389; Gurdon, J. B., (1992) *Cell* 68: 185–199; Jessell, T. M. et al., (1992) *Cell* 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68: 185–199).

Members of the hedgehog family of signaling molecules mediate many important short- and long-range patterning processes during invertebrate and vertebrate development. In the fly, a single hedgehog gene regulates segmental and imaginal disc patterning. In contrast, in vertebrates, a hedgehog gene family is involved in the control of left-right asymmetry, polarity in the CNS, somites and limb, organogenesis, chondrogenesis and spermatogenesis.

Recent evidence suggests a model in which hedgehog signaling plays a crucial role in the regulation of chondrogenic development (Roberts et al. (1995) supra). During cartilage formation, chondrocytes proceed from a proliferating state via an intermediate, prehypertrophic state to differentiated hypertrophic chondrocytes. Ihh is expressed in the prehypertrophic chondrocytes and initiates a signaling cascade that leads to the blockage of chondrocyte differentiation. Its direct target is the perichondrium around the Ihh expression domain, which responds by the expression of gli and patched (Ptc), conserved transcriptional targets of hedgehog signaling (see below). Most likely, this leads to secondary signaling resulting in the synthesis of parathyroid hormone-related protein (PTHrP) in the periarticular perichondrium. PTHrP itself signals back to the prehypertrophic chondrocytes, blocking their further differentiation. At the same time, PTHrP represses expression of Ihh, thereby forming a negative feedback loop that modulates the rate of chondrocyte differentiation.

Although Ihh is expressed in a pattern consistent with a role in regulating cartilage development in the context of normal development, recent studies demonstrate that all of the identified hedgehog family members behave similarly in a variety of cell culture and tissue assays (Pathi et al., 2001). This indicates that the hedgehog signaling pathway is highly conserved, and that the various hedgehog family members activate the same cascade of downstream genes. The apparent differences between the hedgehog family members is likely due to their differential expression, and the presence of other regulatory proteins expressed during embryogenesis.

Cartilage Disorders

Cartilage is a hyperhydrated structure with water comprising 70% to 80% of its weight. The remaining 20% to 30% comprises collagen (primarily type-II) and proteoglycan with collagen typically accounting for 70% of the dry weight of cartilage (in "Pathology" (1988) Eds. Rubin & Farber, J. B. Lippincott Company, PA. pp. 1369–1371). Proteoglycans are composed of a central protein core from which long chains of polysaccharides extend. These polysaccharides, called glycosaminoglycans, include: chondroitin-4-sulfate; chondroitin-6-sulfate; and keratan sulfate. Cartilage has a characteristic structural organization consisting of chondrogenic cells dispersed within an endogenously produced and secreted extracellular matrix. The cavities in the matrix which contain the chondrocytes are called cartilage lacunae. Unlike bone, cartilage is neither innervated nor penetrated by either the vascular or lymphatic systems (Clemente (1984) in "Gray's Anatomy, $30^{th}$ Edit," Lea & Febiger).

Three types of cartilage are present in mammals and include: hyaline cartilage, fibrocartilage, and elastic cartilage (Rubin and Farber, supra). Hyaline cartilage consists of a gristly mass having a firm, elastic consistency, is translucent and is pearly blue in color. Hyaline cartilage is predominantly found on the articulating surfaces of articulating joints. It is found also in epiphyseal plates, costal cartilage, tracheal cartilage, bronchial cartilage and nasal cartilage. Fibrocartilage is essentially the same as hyaline cartilage except that it contains fibrils of type I collagen that add tensile strength to the cartilage. The collagenous fibers are arranged in bundles, with the cartilage cells located between the bundles. Fibrocartilage is found commonly in the anulus fibrosus of the invertebral disc, tendinous and ligamentous insertions, menisci, the symphysis pubis, and insertions of joint capsules. Elastic cartilage also is similar to hyaline cartilage except that it contains fibers of elastin. It is more opaque than hyaline cartilage and is more flexible and pliant. These characteristics are defined in part by the elastic fibers embedded in the cartilage matrix. Typically, elastic cartilage is present in the pinna of the ears, the epiglottis, and the larynx.

The surfaces of articulating bones in mammalian joints are covered with articular cartilage. The articular cartilage prevents direct contact of the opposing bone surfaces and permits the near frictionless movement of the articulating bones relative to one another (Clemente, supra).

Two types of articular cartilage defects are commonly observed in mammals and include full-thickness and partial-thickness defects. The two types of defects differ not only in the extent of physical damage but also in the nature of repair response each type of lesion elicits.

Full-thickness articular cartilage defects include damage to the articular cartilage, the underlying subchondral bone tissue, and the calcified layer of cartilage located between the articular cartilage and the subchondral bone. Full-thickness defects typically arise during severe trauma of the joint or during the late stages of degenerative joint diseases, for example, during osteoarthritis. Since the subchondral bone tissue is both innervated and vascularized, damage to this tissue is often painful. The repair reaction induced by damage to the subchondral bone usually results in the formation of fibrocartilage at the site of the full-thickness defect. Fibrocartilage, however, lacks the biomechanical properties of articular cartilage and fails to persist in the joint on a long term basis.

Partial-thickness articular cartilage defects are restricted to the cartilage tissue itself. These defects usually include fissures or clefts in the articulating surface of the cartilage. Partial-thickness defects are caused by mechanical arrangements of the joint which in turn induce wearing of the cartilage tissue within the joint. In the absence of innervation and vasculature, partial-thickness defects do not elicit repair responses and therefore tend not to heal. Although painless, partial-thickness defects often degenerate into full-thickness defects.

Repair of articular cartilage defects with suspensions of isolated chondrocytes has been attempted in a variety of animal models. See for example: Bentley, et al. (1971) Nature 230: 385–388; Langer et al. (1974) J. Bone Joint Surg. 56A: 297–304; Green (1977) Clin. Orthop. 124: 237–250; and Aston et al. (1986) J. Bone Joint Surg. 68B: 29–35). During transplantation, the cell suspensions may be retained in the defect behind a piece of periosteal tissue that has been previously attached to the surface of the normal cartilage tissue. The rate of successful implantation using cell suspensions was found to be about 40%. It is believed that chondrocytes transplanted in this manner lose their viability during transplantation and that the procedure may result in the formation of fibrocartilage or islands of cartilage embedded in fibrous tissue at the site of the defect.

Three alternative approaches have been developed in an attempt to improve the success rate in treating mammalian articular cartilage defects. In the first approach, synthetic carriers containing dispersed allogeneic chondrocytes may be implanted into the cartilage defect. The implanted chondrocytes hopefully produce and secrete components of the extracellular matrix thereby forming articular cartilage at the site of the defect in situ. In the second approach, synthetic carriers containing chemotactic and mitogenic growth factors may be implanted into the cartilage defect. The growth factors hopefully induce the influx into, and the proliferation of chondrocyte progenitor cells within the matrix. The chondrocyte progenitor cells differentiate subsequently into chondrocytes that in turn secrete components of the extracellular matrix thereby to form articular cartilage at the site of the defect in situ. In the third approach, synthetic cartilage tissue may be grown in vitro and implanted subsequently into the cartilage defect.

In the first approach, the synthetic carriers or biological resorbable immobilization vehicles may be impregnated with allogeneic chondrocytes. A variety of synthetic carriers have been used to date and include: three-dimensional collagen gels (U.S. Pat. No. 4,846,835; Nishimoto (1990) Med. J. Kinki University 15: 75–86; Nixon et al. (1993) Am. J. Vet. Res. 54: 349–356; Wakitani et al. (1989) J. Bone Joint Surg. 71B: 74–80; Yasui (1989) J. Jpn. Ortho. Assoc. 63: 529–538); reconstituted fibrin-thrombin gels (U.S. Pat. No. 4,642,120; U.S. Pat. No. 5,053,050 and U.S. Pat. No. 4,904,259); synthetic polymer matrices containing polyanhydride, polyorthoester, polyglycolic acid and copolymers thereof (U.S. Pat. No. 5,041,138); and hyaluronic acid-based polymers (Robinson et al. (1990) Calcif. Tissue Int. 46: 246–253).

The introduction of non-autologous materials into a patient, however, may stimulate an undesirable immune response directed against the implanted material. Such an immune response has been observed in rabbit models (Yoshinao (1990) J. Jpn. Orth. Assoc. 64: 835–846). In addition, there is evidence to suggest that neo-cartilage may be formed around the periphery of the implant thereby preventing integration of the implant into the cartilage defect. See for example, Messner (1994) $40^{th}$ Annual Meeting Orth. Res. Soc., New Orleans p. 239; and Nixon et al. (1994) $40^{th}$ Annual Meeting Orth. Res. Soc., New Orleans p. 241. Monitoring the formation and development of the resulting synthetic cartilage in situ can be difficult to perform and usually involves an arthroscopic or open joint examination. Furthermore, implants containing synthetic polymer components may be unsuitable for repairing large cartilage defects since polymer hydrolysis in situ may inhibit the formation of cartilage and/or its integration into the defect.

In the second approach, the defect may be filled with a biocompatible, biodegradable carrier containing growth factors to stimulate the influx of chondrocyte progenitor cells in situ. The carriers optimally contain pores of sufficient dimensions to permit the influx into, and proliferation of the chondrocyte progenitors. The carrier also may contain additional growth factors to stimulate the differentiation of chondrocyte progenitor cells into chondrocytes. The resulting chondrocytes hopefully secrete extracellular matrix components thereby to form cartilage at the site of the defect in situ. See for example, U.S. Pat. No. 5,206,023; U.S. Pat. No. 5,270,300; and EP 05 30 804 A1. This approach, however, may have problems similar to those associated with the first approach, hereinabove.

In the third approach, chondrocytes may be cultured in vitro thereby to form synthetic cartilage-like material. The resulting cartilage may be implanted subsequently into the cartilage defect. This type of approach has the advantage over the previous methods in that the development of the synthetic cartilage material may be monitored prior to implantation. In addition, the resulting cartilage may be characterized biochemically and morphologically prior to implantation. Two general procedures have been developed for growing synthetic cartilage in vitro. These include growing chondrogenic cells in either an anchorage-dependent or an anchorage-independent manner.

However, chondrocyte culture is made difficult by the fact that chondrocytes are known to undergo apoptosis in the absence of chemical signals secreted by other chondrocytes. (Y. Ishizaki et al. (1994) J. Cell. Biol. 126: 1069–1077). Thus, high-density chondrocyte cultures are capable of survival, but low-density cultures tend to undergo programmed cell death. Culture medium from high-density cultures can be used to foster survival in low-density cultures, indicating that chemical secretions in the medium are responsible for discouraging apoptosis, although the compounds responsible have not been identified. In addition to confounding in vitro culturing of chondrocytes, this sensitivity to the chemical signalling may underlie certain difficulties encountered in cartilage repair in living animals as well.

SUMMARY OF THE INVENTION

Cartilage related injuries and degenerative diseases impact a cross section of the population, and exact a large price on the quality of life of the sufferers. From sports related injuries that prevent people from enjoying active lives to degenerative diseases that affect even relatively low impact activities like walking or typing, the need for improved treatment for the range of cartilage related conditions exists. The successful reduction of the impact of such injuries and degenerative diseases on the quality of life of patients has tremendous societal benefits.

Currently, there are several treatment options for individuals suffering from conditions of cartilage injury or disease. However, all of these treatments have significant limitations. Two serious limitations are the ability to generate a vast supply of replacement cartilage, and the ability of such replacement cartilage to most closely mimic the endogenous, damaged cartilage. The present invention offers methods and compositions to address these and other limitations not satisfied by the prior art. The present invention provides methods and compositions to promote the production of three dimensional cartilage matrices from cells in culture. These three dimensional matrices are more like endogenous cartilage, and thus the transplantation of such tissue to patients offers a better outcome than the transplantation of other cartilaginous tissue. Additionally, since the three dimensional cartilage matrices of the invention can be produced from cells in culture, including stem cells, they offer a seemingly endless supply of replacement cartilage. Thus, the present invention overcomes many of the shortcomings of the prior art.

The present invention provides methods for using hedgehog, alone or in combination with a TGFβ family member, to form three-dimensional cartilage matrices from chondrocytes or chondrogenic progenitor cells. Such methods provide improved tissues for use in cartilage transplantation therapies, and offer critical options for patients suffering from conditions of cartilage injury, deterioration, or damage. The three-dimensional matrices of the present invention can themselves be used to treat patients, or may be further configured into preferred shapes and sizes using a synthetic carrier or scaffolding.

In one aspect, the invention provides a method for promoting the growth of chondrocytes or chondrogenic progenitor cells to form a three dimensional cartilage matrix by contacting the cells with a hedgehog polypeptide, or functional fragments thereof.

In one embodiment, the chondrocytes or chondrogenic progenitor cells are cells in culture. Preferably the cells in culture are derived from a mammal. More preferably the cells in culture are derived from a human.

In another embodiment, the cells in culture are selected from embryonic stem cells, adult stem cells, fibroblasts, and primary chondrocytes.

In another embodiment, the adult stem cells are selected from mesenchymal stem cells, neural stem cells, hematopoietic stem cells, and skin-derived progenitor cells.

In a second aspect, the invention provides a method for promoting the growth of chondrocytes or chondrogenic progenitor cells to form a three dimensional cartilage matrix by contacting the cells with a hedgehog polypeptide and a TGFβ polypeptide, or functional fragments thereof.

In one embodiment, the chondrocytes or chondrogenic progenitor cells are cells in culture. Preferably the cells in culture are derived from a mammal. More preferably the cells in culture are derived from a human.

In another embodiment, the cells in culture are selected from embryonic stem cells, adult stem cells, fibroblasts, and primary chondrocytes.

In another embodiment, the adult stem cells are selected from mesenchymal stem cells, neural stem cells, hematopoietic stem cells, and skin-derived progenitor cells.

In another embodiment, the hedgehog polypeptide and the TGFβ polypeptide are co-administered.

In another embodiment, the hedgehog polypeptide and the TGFβ polypeptide are administered at different times.

In a third aspect, the invention provides a method for promoting the growth of chondrocytes or chondrogenic progenitor cells to form a three dimensional cartilage matrix by contacting the cells with at least one hedgehog therapeutic.

In one embodiment, the chondrocytes or chondrogenic progenitor cells are cells in culture. Preferably the cells in culture are derived from a mammal. More preferably the cells in culture are derived from a human.

In another embodiment, the cells in culture are selected from embryonic stem cells, adult stem cells, fibroblasts, and primary chondrocytes.

In another embodiment, the adult stem cells are selected from mesenchymal stem cells, neural stem cells, hematopoietic stem cells, and skin-derived progenitor cells.

In another embodiment, the cells are treated with more than one hedgehog therapeutic. In one embodiment, the hedgehog therapeutics are co-administered. In another embodiment, the hedgehog therapeutics are administered at different times.

In another embodiment, at least one hedgehog therapeutic binds to patched and increases expression of patched and/or gli.

In another embodiment, at least one hedgehog therapeutic is a small organic molecule which stimulates hedgehog signaling.

In another embodiment, at least one hedgehog therapeutic alters the localization, protein-protein binding and/or enzymatic activity of an intracellular protein involved in hedgehog signaling.

In another embodiment, at least one hedgehog therapeutic alters the level of expression of a hedgehog protein, a patched protein, or a protein involved in hedgehog signaling.

In a fourth aspect, the invention provides a method for promoting cell migration, proliferation, and differentiation of chondrocytes or chondrogenic precursors to form a three dimensional cartilage matrix by contacting the cells with a hedgehog polypeptide, or functional fragments thereof.

In one embodiment, the chondrocytes or chondrogenic progenitor cells are cells in culture. Preferably the cells in culture are derived from a mammal. More preferably the cells in culture are derived from a human.

In another embodiment, the cells in culture are selected from embryonic stem cells, adult stem cells, fibroblasts, and primary chondrocytes.

In another embodiment, the adult stem cells are selected from mesenchymal stem cells, neural stem cells, hematopoictic stem cells, and skin-derived progenitor cells.

In a fifth aspect, the invention provides a method for promoting cell migration, proliferation, and differentiation of chondrocytes or chondrogenic precursors to form a three dimensional cartilage matrix by contacting the cells with a hedgehog polypeptide and a TGFβ polypeptide, or functional fragments thereof.

In one embodiment, the chondrocytes or chondrogenic progenitor cells are cells in culture. Preferably the cells in culture are derived from a mammal. More preferably the cells in culture are derived from a human.

In another embodiment, the cells in culture are selected from embryonic stem cells, adult stem cells, fibroblasts, and primary chondrocytes.

In another embodiment, the adult stem cells are selected from mesenchymal stem cells, neural stem cells, hematopoietic stem cells, and skin-derived progenitor cells.

In another embodiment, the hedgehog polypeptide and the TGFβ polypeptide are co-administered.

In another embodiment, the hedgehog polypeptide and the TGFβ polypeptide are administered at different times.

In a sixth aspect, the invention provides a method for promoting cell migration, proliferation, and differentiation of chondrocytes or chondrogenic precursors to form a three dimensional cartilage matrix by contacting the cells with at least one hedgehog therapeutic.

In one embodiment, the chondrocytes or chondrogenic progenitor cells are cells in culture. Preferably the cells in culture are derived from a mammal. More preferably the cells in culture are derived from a human.

In another embodiment, the cells in culture are selected from embryonic stem cells, adult stem cells, fibroblasts, and primary chondrocytes.

In another embodiment, the adult stem cells are selected from mesenchymal stem cells, neural stem cells, hematopoietic stem cells, and skin-derived progenitor cells.

In another embodiment, the cells are treated with one hedgehog therapeutic.

In another embodiment, the hedgehog therapeutic binds to patched and increases expression of patched and/or gli.

In another embodiment, the hedgehog therapeutic is a small organic molecule which stimulates hedgehog signaling.

In another embodiment, the hedgehog therapeutic alters the localization, protein-protein binding and/or enzymatic activity of an intracellular protein involved in hedgehog signaling.

In another embodiment, the hedgehog therapeutic alters the level of expression of a hedgehog protein, a patched protein, or a protein involved in hedgehog signaling.

In another embodiment, the cells are treated with more than one hedgehog therapeutic. The hedgehog therapeutics may be co-administered or administered at different times.

In another embodiment, at least one hedgehog therapeutic binds to patched and increases expression of patched and/or gli.

In another embodiment, at least one hedgehog therapeutic is a small organic molecule which stimulates hedgehog signaling.

In another embodiment, at least one hedgehog therapeutic alters the localization, protein-protein binding and/or enzymatic activity of an intracellular protein involved in hedgehog signaling.

In another embodiment, at least one hedgehog therapeutic alters the level of expression of a hedgehog protein, a patched protein, or a protein involved in hedgehog signaling.

In a seventh aspect, the invention provides a three dimensional cartilage matrix produced by contacting cells with a hedgehog polypeptide, or functional fragments thereof. Preferably the three dimensional cartilage matrix is combined with a pharmaceutically acceptable excipient.

In an eighth aspect, the invention provides a three dimensional cartilage matrix produced by contacting cells with a hedgehog polypeptide and a TGFβ polypeptide, or functional fragments thereof. Preferably the three dimensional cartilage matrix is combined with a pharmaceutically acceptable excipient.

In a ninth aspect, the invention provides a three dimensional cartilage matrix produced by contacting cells with at least one hedgehog therapeutic. Preferably the three dimensional cartilage matrix is combined with a pharmaceutically acceptable excipient.

In a tenth aspect, the invention provides a method for producing a three dimensional cartilage matrix comprising the steps of establishing a culture of cells with cartilage forming potential, and contacting the culture of cells with an amount of a hedgehog polypeptide, or functional fragments thereof, sufficient to induce the growth and differentiation of a three dimensional cartilage matrix.

In one embodiment, the method includes isolating the three dimensional cartilage matrix from the culture of cells.

In another embodiment, the method includes providing a scaffold to influence the shape of the three dimensional cartilage matrix, and isolating the three dimensional cartilage matrix from the culture of cells.

In another embodiment, the method further comprises treating a condition characterized by cartilage loss, damage, or disease by administering a therapeutically effective amount of the isolated three dimensional cartilage matrix to a patient.

In an eleventh aspect, the invention provides a method for producing a three dimensional cartilage matrix comprising the steps of establishing a culture of cells with cartilage forming potential, and contacting the culture of cells with an amount of a hedgehog polypeptide and a TGFβ polypeptide, or functional fragments thereof, sufficient to induce the growth and differentiation of a three dimensional cartilage matrix.

In one embodiment, the method includes isolating the three dimensional cartilage matrix from the culture of cells.

In another embodiment, the method includes providing a scaffold to influence the shape of the three dimensional cartilage matrix, and isolating the three dimensional cartilage matrix from the culture of cells.

In another embodiment, the method further comprises treating a condition characterized by cartilage loss, damage, or disease by administering a therapeutically effective amount of the isolated three dimensional cartilage matrix to a patient.

In another embodiment, the hedgehog polypeptide and the TGFβ polypeptide are co-administered.

In another embodiment, the hedgehog polypeptide and the TGFβ polypeptide are administered at separate times.

In a twelfth aspect, the invention provides a method for producing a three dimensional cartilage matrix comprising the steps of establishing a culture of cells with cartilage forming potential, and contacting the culture of cells with an amount of at least one hedgehog therapeutic sufficient to induce the growth and differentiation of a three dimensional cartilage matrix.

In one embodiment, the method includes isolating the three dimensional cartilage matrix from the culture of cells.

In another embodiment, the method includes providing a scaffold to influence the shape of the three dimensional cartilage matrix, and isolating the three dimensional cartilage matrix from the culture of cells.

In another embodiment, the method further comprises treating a condition characterized by cartilage loss, damage, or disease by administering a therapeutically effective amount of the isolated three dimensional cartilage matrix to a patient.

In a thirteenth aspect, the invention provides a method for producing a three dimensional cartilage matrix comprising the steps of establishing a culture of cells with cartilage forming potential, and contacting the culture of cells with an amount of more than one hedgehog therapeutic sufficient to induce the growth and differentiation of a three dimensional cartilage matrix.

In one embodiment, the method includes isolating the three dimensional cartilage matrix from the culture of cells.

In another embodiment, the method includes providing a scaffold to influence the shape of the three dimensional cartilage matrix, and isolating the three dimensional cartilage matrix from the culture of cells.

In another embodiment, the method further comprises treating a condition characterized by cartilage loss, damage, or disease by administering a therapeutically effective amount of the isolated three dimensional cartilage matrix to a patient.

In another embodiment, the hedgehog therapeutics are co-administered.

In another embodiment, the hedgehog therapeutics are administered at separate times.

In a fourteenth aspect, the invention provides a method for treating a condition characterized by cartilage loss, damage, or disease by administering to a patient a therapeutically effective amount of a three dimensional cartilage matrix. In one embodiment, the three dimensional cartilage matrix is combined with a pharmaceutically acceptable excipient.

In one embodiment, the three dimensional cartilage matrix is produced by contacting chondrocytes or chondrogenic progenitor cells with a hedgehog polypeptide, of functional fragments thereof.

In another embodiment, the three dimensional cartilage matrix is produced by contacting chondrocytes or chondrogenic progenitor cells with a hedgehog polypeptide and a TGFβ polypeptide, or functional fragments thereof.

In another embodiment, the three dimensional cartilage matrix is produced by contacting chondrocytes or chondrogenic progenitor cells with at least one hedgehog therapeutic.

In a fifteenth aspect, the invention provides a method for treating a condition characterized by cartilage loss, damage, or disease comprising the steps of isolating adult stem cells from a patient, contacting a culture of the adult stem cells with an amount of a hedgehog polypeptide, or functional fragment thereof, sufficient to induce the growth and differentiation of a three dimensional cartilage matrix in the culture of cells, isolating the three dimensional cartilage matrix, and transplanting a therapeutically effective amount of the isolated three dimensional cartilage matrix to a patient.

In one embodiment, the adult stem cells are mesenchymal stem cells.

In one embodiment, the adult stem cells are isolated from the same patient who will subsequently receive the three dimensional cartilage matrix.

In another embodiment, the adult stem cells are isolated from a donor and the three dimensional cartilage matrix is transplanted into a recipient.

In a sixteenth aspect, the invention provides a method for treating a condition characterized by cartilage loss, damage, or disease comprising the steps of isolating adult stem cells from a patient, contacting a culture of the adult stem cells with an amount of a hedgehog polypeptide and a TGFβ polypeptide, or functional fragment thereof, sufficient to induce the growth and differentiation of a three dimensional cartilage matrix in the culture of cells, isolating the three dimensional cartilage matrix, and transplanting a therapeutically effective amount of the isolated three dimensional cartilage matrix to a patient.

In one embodiment, the adult stem cells are mesenchymal stem cells.

In one embodiment, the adult stem cells are isolated from the same patient who will subsequently receive the three dimensional cartilage matrix.

In another embodiment, the adult stem cells are isolated from a donor and the three dimensional cartilage matrix is transplanted into a recipient.

In a seventeenth aspect, the invention provides a method for treating a condition characterized by cartilage loss, damage, or disease comprising the steps of isolating adult stem cells from a patient, contacting a culture of the adult stem cells with an amount of at least one hedgehog therapeutic sufficient to induce the growth and differentiation of a three dimensional cartilage matrix in the culture of cells, isolating the three dimensional cartilage matrix, and transplanting a therapeutically effective amount of the isolated three dimensional cartilage matrix to a patient.

In one embodiment, the adult stem cells are mesenchymal stem cells.

In one embodiment, the adult stem cells are isolated from the same patient who will subsequently receive the three dimensional cartilage matrix.

In another embodiment, the adult stem cells are isolated from a donor and the three dimensional cartilage matrix is transplanted into a recipient.

In an eighteenth aspect, the invention provides a method for treating a condition characterized by cartilage loss, damage, or disease comprising the steps of isolating adult stem cells from a patient, contacting a culture of the adult stem cells with an amount of more than one hedgehog therapeutic sufficient to induce the growth and differentiation of a three dimensional cartilage matrix in the culture of cells, isolating the three dimensional cartilage matrix, and transplanting a therapeutically effective amount of the isolated three dimensional cartilage matrix to a patient.

In one embodiment, the adult stem cells are mesenchymal stem cells.

In one embodiment, the adult stem cells are isolated from the same patient who will subsequently receive the three dimensional cartilage matrix.

In another embodiment, the adult stem cells are isolated from a donor and the three dimensional cartilage matrix is transplanted into a recipient.

In a nineteenth aspect, the invention provides a kit for the production of a three dimensional cartilage matrix, comprising a hedgehog polypeptide combined with a pharmaceutically acceptable excipient; instructions for using the hedgehog polypeptide to promote the formation of a three dimensional cartilage matrix; and a synthetic scaffold to influence the shape of the three dimensional cartilage matrix. In one embodiment, the scaffold comprises precursors necessary for generating a biopolymer carrier or scaffold.

In a twentieth aspect, the invention provides a kit for the production of a three dimensional cartilage matrix, comprising a hedgehog polypeptide and a TGFβ polypeptide combined with a pharmaceutically acceptable excipient; instructions for using the hedgehog polypeptide and the TGFβ polypeptide to promote the formation of a three dimensional cartilage matrix; and a synthetic scaffold to influence the shape of the three dimensional cartilage matrix. In one embodiment, the scaffold comprises precursors necessary for generating a biopolymer carrier or scaffold.

In a twenty first aspect, the invention provides a kit for the production of a three dimensional cartilage matrix, comprising at least one hedgehog therapeutic combined with a pharmaceutically acceptable excipient; instructions for using the hedgehog therapeutic to promote the formation of a three dimensional cartilage matrix; and a synthetic scaffold to influence the shape of the three dimensional cartilage matrix. In one embodiment, the scaffold comprises precursors necessary for generating a biopolymer carrier or scaffold.

In a twenty second aspect, the invention provides a method for conducting a mesenchymal stem cell business, comprising harvesting tissue from tissue typed donors; establishing tissue typed mesenchymal stem cell cultures from the donor tissue; preserving the tissue typed mesenchymal stem cells for later use.

In one embodiment, the harvested tissue is selected from bone marrow, skin, and skeletal muscle.

In another embodiment, the method further comprises retrieving the preserved tissue typed mesenchymal stem cells; and providing said stem cells, to a patient in need thereof.

In another embodiment, the method further includes a system for billing the patient or the patient's insurance provider.

In a twenty third aspect, the invention provides a method for conducting a regenerative cartilage business, comprising harvesting tissue from tissue typed donors; establishing mesenchymal stem cell cultures from the harvested tissue; contacting the mesenchymal stem cell culture with an amount of an agent sufficient to promote the formation of three dimensional cartilage matrices from the mesenchymal stem cells; and providing the three dimensional cartilage matrices to a physician or health care provider for transplantation to a patient in need thereof.

In one embodiment, the agent sufficient to promote the formation of three dimensional cartilage matrices is selected from at least one of a hedgehog polypeptide, a hedgehog therapeutic, or a hedgehog polypeptide and a TGFβ polypeptide.

In another embodiment, the harvested tissue is selected from bone marrow, skin, and skeletal muscle.

In another embodiment, the method further comprises banking a portion of the mesenchymal stem cells for later retrieval and use.

In another embodiment, the method further comprises a system for billing a patient or a patient's insurance provider.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986). Other features and advantages of the invention will be apparent from the following detailed description, and from the claims.

BRIEF DESCRIPTION OF THE DRAWINGS

FIG. 2A provides a low power view while FIG. 2B provides a high power view.

FIG. 6 is a table summarizing the results of immunohistochemical analysis performed on paraffin sections of tissue treated with sonic hedgehog and harvested after 21 days.

Figure 1:
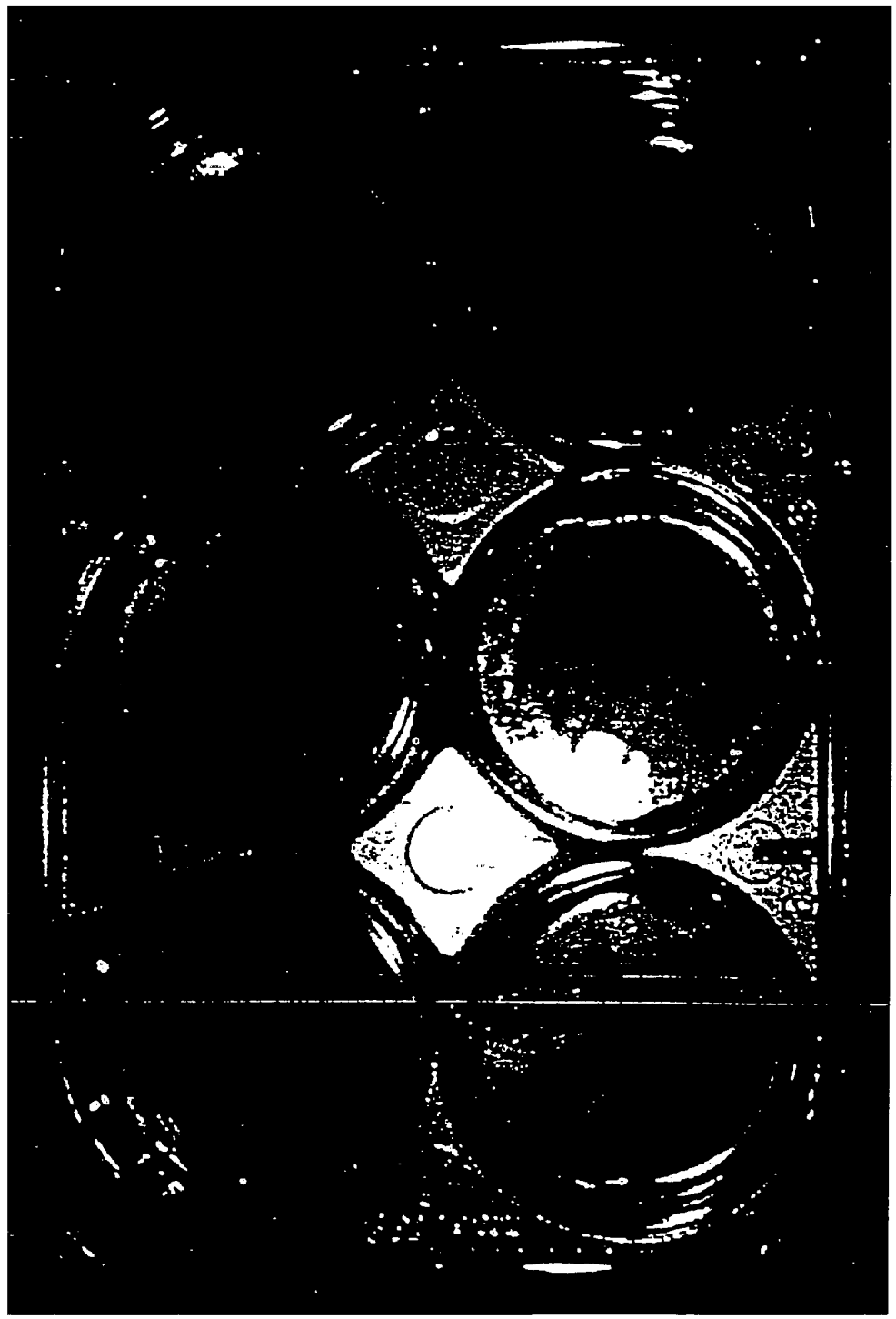
FIG. 1 shows a three week old culture of cells treated with sonic hedgehog protein. Note the tissue which initially formed a monolayer has condensed and migrated to form a small ball loosely attached to only a portion of the well.

Table 1 summarizes the nucleic acid and amino acid sequences provided in the sequence listing.

DETAILED DESCRIPTION OF THE INVENTION

I. Definitions

For convenience, certain terms employed in the specification, examples, and appended claims are collected here.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

As used herein, "proliferating" and "proliferation" refer to cells undergoing mitosis.

As used herein, "chondrogenic progenitor cells" refer to cells with the potential to give rise to chondrocytes under a given set of conditions. The term does not imply that the cells only give rise to chondrocytes, or that the cells give rise to chondrocytes under all experimental conditions.

As used herein, "three dimensional cartilage matrix" refers to the tissue array produced following treatment of cells with chondrogenic potential. This matrix is characterized by a thickness of at least three cell layers, and the expression of markers of cartilage development. The three dimensional cartilage matrix must be positive for at least three markers selected from vimentin protein, collagen II protein, BMPR-IA protein, BMPR-IB protein, BMPR-II protein, and Alcian blue staining.

As used herein, "hedgehog polypeptide" refers to a polypeptide that is a member of the hedgehog family based on sequence, structure, and functional characteristics. Such functional characteristics include the ability to stimulate signaling through the hedgehog signaling pathway and the ability to bind the receptor patched. Amino acid sequences corresponding to exemplary hedgehog polypeptides are provided in SEQ ID NOs: 10–18, and nucleic acid sequences encoding said hedgehog polypeptides are provided in SEQ ID NOs: 1–9.

As used herein the term "approximately 19 kDa" with respect to N-terminal bioactive fragments of a hedgehog protein, refers to a polypeptide which can range in size from 16 kDa to 22 kDa, more preferably 18–20 kDa. In a preferred embodiment, "approximately 19 kDa" refers to a mature form of the peptide after the cleavage of the signal sequence and proteolysis to release an N-terminal portion of the mature protein. Amino acid sequences corresponding to exemplary mature hedgehog polypeptides are provided in SEQ ID NOs: 20–27. SEQ ID NO: 20 provides the amino acid sequence for the mature form of chicken Sonic hedgehog, and this amino acid sequence corresponds to amino acid residues 27–200 of SEQ ID NO: 10. SEQ ID NO: 21 provides the amino acid sequence for the mature form of mouse Desert hedgehog, and this amino acid sequence corresponds to amino acid residues 23–198 of SEQ ID NO: 11. SEQ ID NO: 22 provides the amino acid sequence for the mature form of mouse Indian hedgehog, and this amino acid sequence corresponds to amino acid residues 28–202 of SEQ ID NO: 12. SEQ ID NO: 23 provides the amino acid sequence for the mature form of mouse Sonic hedgehog, and this amino acid sequence corresponds to amino acid residues 25–198 of SEQ ID NO: 13. SEQ ID NO: 24 provides the amino acid sequence for the mature form of zebrafish Sonic hedgehog, and this amino acid sequence corresponds to amino acid residues 24–197 of SEQ ID NO: 14. SEQ ID NO: 25 provides the amino acid sequence for the mature form of human Sonic hedgehog, and this amino acid sequence corresponds to amino acid residues 24–197 of SEQ ID NO: 15. SEQ ID NO: 26 provides the amino acid sequence for the mature form of human Indian hedgehog, and this amino acid sequence corresponds to amino acid residues 28–202 of SEQ ID NO: 16. SEQ ID NO: 27 provides the amino acid sequence for the mature form of human Desert hedgehog, and this amino acid sequence corresponds to amino acid residues 23–198 of SEQ ID NO: 17.

As used herein, the terms "transforming growth factor-beta" and "TGF-β" denote a family of structurally related paracrine polypeptides found ubiquitously in vertebrates, and prototypic of a large family of metazoan growth, differentiation, and morphogenesis factors (see, for review, Massaque et al. (1990) *Ann Rev Cell Biol* 6:597–641; and Sporn et al. (1992) *J Cell Biol* 119:1017–1021). Included in this family are the "bone morphogenetic proteins" or "BMPs", which refers to proteins isolated from bone, and fragments thereof and synthetic peptides which are capable of inducing bone deposition alone or when combined with appropriate cofactors. Preparations of BMPs, such as BMP-1, -2, -3, and -4, are described in, for example, PCT publication WO 88/00205. Wozney (1989) *Growth Fact Res* 1:267–280 describes additional BMP proteins closely related to BMP-2, and which have been designated BMP-5, -6, and -7. PCT publications WO89/09787 and WO89/09788 describe a protein called "OP-1," now known to be BMP-7. Other BMPs are known in the art.

As used herein, "hedgehog therapeutic" refers to polypeptides, nucleic acids, and small molecules that stimulate or antagonize hedgehog signaling. Exemplary hedgehog therapeutics include hedgehog polypeptides, small molecules which bind patched extracellularly and mimic hedgehog signaling, and small molecules which bind a protein involved in the intracellular tranduction of hedgehog signaling.

As used herein, "small organic molecule" refers to compounds smaller than proteins that are generally characterized by the ability to transit cellular membranes more easily than proteins. Preferred small organic molecules are characterized as having a size less than 10,000 AMU. More preferably, between 5000–10,000 AMU. Most preferably, the small organic molecules are characterized as having a size between 1000–5000 AMU.

As used herein, "hedgehog signaling" refers to the hedgehog signaling pathway. This signaling pathway is well known in the art and influences patterning in many developmental contexts. Briefly, hedgehog binds to its receptor patched, thus relieving cells from patched mediated repression. This in turns activates a number of downstream genes including gli and patched itself. It is this activation of downstream gene expression from hedgehog and patched at the cell surface to the nucleus that constitutes hedgehog signaling and the hedgehog signaling pathway.

As used herein, "carrier and scaffold" are used interchangeably and refer to any synthetic or biopolymer array upon which cells can be seeded in order to influence their shape or size. Such carriers or scaffolds may optionally be used as a source of growth factors, cytokines, or other agents. In an illustrative example, a synthetic scaffold or carrier could be loaded with a growth factor, and then seeded with mesenchymal stem cells. The scaffolding would thus serve two functions: a local source of the growth factor, and carrier to influence the shape of the differentiating stem cells.

A "patient" or "subject" to be treated by the subject method can mean either a human or non-human animal, such as a mammal.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be refered to as homologous at that position. A percentage of homology or identity between sequences is a function of the number of matching or homologous positions shared by the sequences.

The terms "recombinant protein", "heterologous protein" and "exogenous protein" are used interchangeably throughout the specification and refer to a polypeptide which is produced by recombinant techniques, wherein generally, a nucleic acid encoding the polypeptide is inserted into a suitable expression construct which is in turn used to transform a host cell to produce the heterologous protein. That is, the polypeptide is expressed from a heterologous nucleic acid.

A "chimeric protein" or "fusion protein" is a fusion of a first amino acid sequence encoding a hedgehog polypeptide with a second amino acid sequence defining a domain foreign to and not substantially homologous with any domain of hh protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula $(X)_n$-$(hh)_m$-$(Y)_n$, wherein hh represents all or a portion of the hedgehog protein, X and Y each independently represent amino acid sequences which are not naturally found as a polypeptide chain contiguous with the hedgehog sequence, m is an integer greater than or equal to 1, and each occurrence of n is, independently, 0 or an integer greater than or equal to 1 (n and m are preferably no greater than 5 or 10).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding one of the vertebrate hh polypeptides of the present invention, including both exon and (optionally) intron sequences. A "recombinant gene" refers to nucleic acid encoding a vertebrate hh polypeptide and comprising vertebrate hh-encoding exon sequences, though it may optionally include intron sequences which are either derived from a chromosomal vertebrate hh gene or from an unrelated chromosomal gene. Exemplary recombinant genes encoding the subject vertebrate hh polypeptide are represented by SEQ ID No: 1, SEQ ID No: 2, SEQ ID No: 3, SEQ ID No: 4, SEQ ID No: 5, SEQ ID No: 6, SEQ ID No: 7, SEQ ID NO: 8 or SEQ ID NO: 9. The term "intron" refers to a DNA sequence present in a given vertebrate hh gene which is not translated into protein and is generally found between exons.

As used herein, the term "transfection" means the introduction of a nucleic acid, e.g., an expression vector, into a recipient cell by nucleic acid-mediated gene transfer.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors".

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant hedgehog genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of hedgehog proteins.

II. Hedgehog Signaling

The first hedgehog gene was identified by a genetic screen in the fruitfly *Drosophila melanogaster* (Nüsslein-Volhard, C. and Wieschaus, E. (1980) *Nature* 287: 795–801). This screen identified a number of mutations affecting embryonic and larval development. In 1992 and 1993, the molecular nature of the *Drosophila* hedgehog (hh) gene was reported (CF., Lee et al. (1992) *Cell* 71: 33–50), and since then, several hedgehog homologues have been isolated from various vertebrate species. While only one hedgehog gene has been found in *Drosophila* and other invertebrates, multiple hedgehog genes are present in vertebrates.

The vertebrate family of hedgehog genes includes at least four members, e.g., paralogs of the single *Drosophila* hedgehog gene. Exemplary hedgehog genes and proteins are described in PCT publications WO 95/18856 and WO 96/17924, the disclosures of which are hereby incorporated by reference in their entirety. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; indian hedgehog (Ihh) is involved in bone development during embryogenesis and in bone formation in the adult; and, Shh, which as described above, is primarily involved in morphogenic and neuroinductive activities. Despite the different roles fulfilled by the hedgehog family members during normal development, they are all capable of performing the same functions. Recent studies by Pathi and colleagues demonstrate that sonic hedgehog, desert hedgehog, and indian hedgehog all bind the receptor patched with the same kinetics. Additionally, the three hedgehog family members affect cell fate and behavior in the same way, albeit with differing potencies in a range of cell and tissue based assays (Pathi et al. (2001) Mechanisms of Development).

The various hedgehog proteins consist of a signal peptide, a highly conserved N-terminal region, and a more divergent C-terminal domain. In addition to signal sequence cleavage in the secretory pathway (Lee, J. J. et al. (1992) *Cell* 71: 33–50; Tabata, T. et al. (1992) *Genes Dev.* 2635–2645; Chang, D. E. et al. (1994) *Development* 120:3 339–3353), hedgehog precursor proteins undergo an internal autoproteolytic cleavage which depends on conserved sequences in the C-terminal portion (Lee et al. (1994) *Science* 266: 1528–1537; Porter et al. (1995) *Nature* 374: 363–366). This autocleavage leads to a 19 kD N-terminal peptide and a C-terminal peptide of 26–28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15: 2294–2303; Porter et al. (1995) supra; Ekker, S. C. et al. (1995) *Curr. Biol.* 5: 944–955; Lai, C. J. et al (1995) *Development* 121: 2349–2360). The N-terminal peptide stays tightly associated with the surface of cells in which it was synthesized, while the C-terminal peptide is freely diffusible both in vitro and in vivo (Porter et al. (1995) *Nature* 374: 363; Lee et al. (1994) supra; Bumcrot et al. (1995) supra; Mart', E. et al. (1995) *Development* 121: 2537–2547; Roelink, H. et al. (1995) *Cell* 81: 445–455). Interestingly, cell surface retention of the N-terminal peptide is dependent on autocleavage, as a truncated form of hedgehog protein encoded by an RNA which terminates precisely at the normal position of internal cleavage is diffusible in vitro (Porter et al. (1995) supra) and in vivo (Porter, J. A. et al. (1996) *Cell* 86: 21–34). Biochemical studies have shown that the autoproteolytic cleavage of the hedgehog precursor protein proceeds through an internal thioester intermediate which subsequently is cleaved in a nucleophilic substitution. It is likely that the nucleophile is a small lipophilic molecule which becomes covalently bound to the C-terminal end of the N-peptide (Porter et al. (1996) supra), tethering it to the cell surface. The biological implications are profound. As a result of the tethering, a high local concentration of N-terminal hedgehog peptide is generated on the surface of the hedgehog producing cells. It is this N-terminal peptide which is both necessary and sufficient for short- and long-range hedgehog signaling activities in *Drosophila* and vertebrates (Porter et al. (1995) supra; Ekker et al. (1995) supra; Lai et al. (1995) supra; Roelink, H. et al. (1995) *Cell* 81: 445–455; Porter et al. (1996) supra; Fietz, M. J. et al. (1995) *Curr. Biol.* 5: 643–651; Fan, C.-M. et al. (1995) *Cell* 81: 457–465; Mart', E., et al (1995) *Nature* 375: 322–325; Lopez-Martinez et al. (1995) *Curr. Biol* 5: 791–795; Ekker, S. C. et al. (1995) *Development* 121: 2337–2347; Forbes, A. J. et al.(1996) *Development* 122: 1125–1135).

Hedgehog has been implicated in short- and long-range patterning processes at various sites during *Drosophila* development. In the establishment of segment polarity in early embryos, it has short-range effects which appear to be directly mediated, while in the patterning of the imaginal discs, it induces long range effects via the induction of secondary signals.

In vertebrates, several hedgehog genes have been cloned in the past few years. Of these genes, Shh has received most of the experimental attention, as it is expressed in different organizing centers which are the sources of signals that pattern neighboring tissues. Recent evidence indicates that Shh is involved in these interactions.

The expression of Shh starts shortly after the onset of gastrulation in the presumptive midline mesoderm, the node in the mouse (Chang et al. (1994) supra; Echelard, Y. et al. (1993) *Cell* 75: 1417–1430), the rat (Roelink, H. et al. (1994) *Cell* 76: 761–775) and the chick (Riddle, R. D. et al. (1993) *Cell* 75: 1401–1416), and the shield in the zebrafish (Ekker et al. (1995) supra; Krauss, S. et al.(1993) *Cell* 75: 1431–1444). In chick embyros, the Shh expression pattern in the node develops a left-right asymmetry, which appears to be responsible for the left-right situs of the heart (Levin, M. et al. (1995) *Cell* 82: 803–814).

In the CNS, Shh from the notochord and the Doorplate appears to induce ventral cell fates. When ectopically expressed, Shh leads to a ventralization of large regions of the mid- and hindbrain in mouse (Echelard et al. (1993) supra; Goodrich, L. V. et al. (1996) *Genes Dev.* 10:301–312), Xenopus (Roelink, H. et al. (1994) supra; Ruiz i Altaba, A. et al. (1995) *Mol. Cell. Neurosci.* 6:106–121), and zebrafish (Ekker et al. (1995) supra; Krauss et al. (1993) supra; Hammerschmidt, M., et al. (1996) *Genes Dev.* 10:647–658). In explants of intermediate neuroectoderm at spinal cord levels, Shh protein induces Doorplate and motor neuron development with distinct concentration thresholds, floor plate at high and motor neurons at lower concentrations (Roelink et al. (1995) supra; Mart'et al. (1995) supra; Tanabe, Y. et al. (1995) *Curr. Biol.* 5:651–658). Moreover, antibody blocking suggests that Shh produced by the notochord is required for notochord-mediated induction of motor neuron fates (Mart'et al. (1995) supra). Thus, high concentration of Shh on the surface of Shh-producing midline cells appears to account for the contact-mediated induction of Doorplate observed in vitro (Placzek, M. et al. (1993) *Development* 117:205–218), and the midline positioning of the Doorplate immediately above the notochord in vivo. Lower concentrations of Shh released from the notochord and the Doorplate presumably induce motor neurons at more distant ventrolateral regions in a process that has been shown to be contact-independent in vitro (Yamada, T. et al. (1993) *Cell* 73:673–686). In explants taken at midbrain and forebrain levels, Shh also induces the appropriate ventrolateral neuronal cell types, dopaminergic (Heynes, M. et al. (1995) *Neuron* 15:35–44; Wang, M. Z. et al. (1995) *Nature Med.* 1:1184–1188) and cholinergic (Ericson, J. et al. (1995) *Cell* 81:747–756) precursors, respectively, indicating that Shh is a common inducer of ventral specification over the entire length of the CNS. These observations raise a question as to how the differential response to Shh is regulated at particular anteroposterior positions.

Shh from the midline also patterns the paraxial regions of the vertebrate embryo, the somites in the trunk (Fan et al. (1995) supra) and the head mesenchyme rostral of the somites (Hammerschmidt et al. (1996) supra). In chick and mouse paraxial mesoderm explants, Shh promotes the expression of sclerotome specific markers like Pax1 and Twist, at the expense of the dermamyotomal marker Pax3. Moreover, filter barrier experiments suggest that Shh mediates the induction of the sclerotome directly rather than by activation of a secondary signaling mechanism (Fan, C.-M. and Tessier-Lavigne, M. (1994) *Cell* 79, 1175–1186).

Shh also induces myotomal gene expression (Hammerschmidt et al. (1996) supra; Johnson, R. L. et al. (1994) *Cell* 79:1165–1173; Münsterberg, A. E. et al. (1995) *Genes Dev.* 9:2911–2922; Weinberg, E. S. et al. (1996) *Development* 122:271–280), although recent experiments indicate that members of the WNT family, vertebrate homologues of *Drosophila wingless,* are required in concert (Münsterberg et al. (1995) supra). Puzzlingly, myotomal induction in chicks requires higher Shh concentrations than the induction of sclerotomal markers (Münsterberg et al. (1995) supra), although the sclerotome originates from somitic cells positioned much closer to the notochord. Similar results were obtained in the zebrafish, where high concentrations of hedgehog induce myotomal and repress sclerotomal marker gene expression (Hammerschmidt et al. (1996) supra). In contrast to amniotes, however, these observations are consistent with the architecture of the fish embryo, as here, the myotome is the predominant and more axial component of the somites. Thus, modulation of Shh signaling and the acquisition of new signaling factors may have modified the somite structure during vertebrate evolution.

Figure 2A:
FIGS. 2A–2B show light microscopic analysis of hematoximine-eosine stained paraffin sections of tissue treated with sonic hedgehog and harvested after 21 days. Note the extensive organization of the tissue, the intricate folding of the layers, and the abundant matrix production.

In the vertebrate limb buds, a subset of posterior mesenchymal cells, the "Zone of polarizing activity" (ZPA), regulates anteroposterior digit identity (reviewed in Honig, L. S. (1981) *Nature* 291:72–73). Ectopic expression of Shh or application of beads soaked in Shh peptide mimics the effect of anterior ZPA grafts, generating a mirror image duplication of digits (Chang et al. (1994) supra; Lopez-Martinez et al. (1995) supra; Riddle et al. (1993) supra) (FIG. 2g). Thus, digit identity appears to depend primarily on Shh concentration, although it is possible that other signals may relay this information over the substantial distances that appear to be required for AP patterning (100–150 μm). Similar to the interaction of HH and DPP in the *Drosophila* imaginal discs, Shh in the vertebrate limb bud activates the expression of Bmp2 (Francis, P. H. et al. (1994) *Development* 120:209–218), a dpp homologue. However, unlike DPP in *Drosophila*, Bmp2 fails to mimic the polarizing effect of Shh upon ectopic application in the chick limb bud (Francis et al. (1994) supra). In addition to anteroposterior patterning, Shh also appears to be involved in the regulation of the proximodistal outgrowth of the limbs by inducing the synthesis of the fibroblast growth factor FGF4 in the posterior apical ectodermal ridge (Laufer, E. et al. (1994) *Cell* 79:993–1003; Niswander, L. et al.(1994) *Nature* 371:609–612).

The close relationship between hedgehog proteins and BMPs is likely to have been conserved at many, but probably not all sites of vertebrate hedgehog expression. For example, in the chick hindgut, Shh has been shown to induce the expression of Bmp4, another vertebrate dpp homologue (Roberts, D. J. et al. (1995) *Development* 121:3163–3174). Furthermore, Shh and Bmp2, 4, or 6 show a striking correlation in their expression in epithelial and mesenchymal cells of the stomach, the urogenital system, the lung, the tooth buds and the hair follicles (Bitgood, M. J. and McMahon, A. P. (1995) *Dev. Biol.* 172:126–138). Further, Ihh, one of the two other mouse hedgehog genes, is expressed adjacent to Bmp expressing cells in the gut and developing cartilage (Bitgood and McMahon (1995) supra).

Recent evidence suggests a model in which Ihh plays a crucial role in the regulation of chondrogenic development (Roberts et al. (1995) supra). During cartilage formation, chondrocytes proceed from a proliferating state via an intermediate, prehypertrophic state to differentiated hypertrophic chondrocytes. Ihh is expressed in the prehypertrophic chondrocytes and initiates a signaling cascade that leads to the blockage of chondrocyte differentiation. Its direct target is the perichondrium around the Ihh expression domain, which responds by the expression of gli and patched (Ptc), conserved transcriptional targets of hedgehog signals (see below). Most likely, this leads to secondary signaling resulting in the synthesis of parathyroid hormone-related protein (PTHrP) in the periarticular perichondrium. PTHrP itself signals back to the prehypertrophic chondrocytes, blocking their further differentiation. At the same time, PTHrP represses expression of Ihh, thereby forming a negative feedback loop that modulates the rate of chondrocyte differentiation.

Patched was originally identified in Drosophila as a segment polarity gene, one of a group of developmental genes that affect cell differentiation within the individual segments that occur in a homologous series along the anterior-posterior axis of the embryo. See Hooper, J. E. et al. (1989) *Cell* 59: 751; and Nakano, Y. et al. (1989) *Nature* 341: 508. Patterns of expression of the vertebrate homologue of patched suggest its involvement in the development of neural tube, skeleton, limbs, craniofacial structure, and skin.

Genetic and functional studies demonstrate that patched is part of the hedgehog signaling cascade, an evolutionarily conserved pathway that regulates expression of a number of downstream genes. See Perrimon, N. (1995) *Cell* 80: 517; and Perrimon, N. (1996) *Cell* 86: 513. Patched participates in the constitutive transcriptional repression of the target genes; its effect is opposed by a secreted glycoprotein, encoded by hedgehog, or a vertebrate homologue, which induces transcriptional activation. Genes under control of this pathway include members of the Wnt and TGF-beta families.

Patched proteins possess two large extracellular domains, twelve transmembrane segments, and several cytoplasmic segments. See Hooper, supra; Nakano, supra; Johnson, R. L. et al. (1996) *Science* 272: 1668; and Hahn, H. et al. (1996) *Cell* 85: 841. In the absence of hedgehog protein, patched is believed to function as a repressor which inhibits hedgehog mediated signal transduction. Hedgehog protein binds to patched and relieves this patched mediated repression. A second transmembrane protein encoded by the smoothened gene is also involved in hedgehog signal transduction, however, the exact biochemical role of smoothened in hedgehog signaling is not clear. The binding of hedgehog protein to patched, and the relief of patched mediated repression, activates the hedgehog signaling pathway. Several downstream genes, including patched itself and gli, are activated in response to hedgehog signaling and act to transduce the hedgehog signal from the cell membrane to the nucleus.

The present invention provides methods for promoting the formation of three dimensional cartilage matrices from chondrocytes and chondrogenic progenitor cells by stimulating hedgehog signaling. Stimulation of hedgehog signaling is attained by contacting cells with nucleic acids, polypeptides, or small organic molecules that stimulate hedgehog signaling.

In one embodiment, hedgehog signaling is stimulated by contacting cells with a hedgehog polypeptide. Recent evidence confirms that any of the hedgehog polypeptides can stimulate hedgehog signaling and have similar affects in a variety of target tissues (Pathi et al. (2001) supra). Preferred hedgehog polypeptides are encoded by nucleic acids comprising an amino acid sequence at least 60% identical, more preferably 70% identical, and most preferably 80% identical with a vertebrate hedgehog polypeptide, or bioactive fragement thereof. Nucleic acids which encode polypeptides at least about 90%, more preferably at least about 95%, and most preferably at least about 98–99% identical with a vertebrate hedgehog polypeptide, or bioactive fragment thereof, are also within the scope of the invention.

In another embodiment, hedgehog signaling is stimulated by contacting cells with one or more hedgehog therapeutic. Such hedgehog therapeutics may stimulate hedgehog signaling by impinging upon the hedgehog signaling pathway at any point in the pathway. One of skill will recognize that such hedgehog therapeutics include nucleic acids, polypeptides, and small molecules that stimulate hedgehog signaling by acting at any point in the hedgehog pathway. Exemplary hedgehog therapeutics include small molecules that bind to patched and simulate hedgehog mediated signaling and small molecules that stimulate hedgehog signaling downstream of patched, thus by-passing the need to relieve patched mediated repression of hedgehog signaling.

In another aspect, the present invention provides methods for promoting the formation of three dimensional cartilage matrices from chondrocytes and chondrogenic progenitor cells by stimulating hedgehog signaling and TGFβ signaling. TGFβ family members are co-expressed with hedgehog family members in many tissues, and in many systems hedgehog signaling activates expression of a TGFβ family member. Therefore, the present invention provides methods to augment the increase in TGFβ signaling typically observed in the presence of hedgehog signaling. The hedgehog polypeptide or therapeutic can be administered in combination with the TGFβ polypeptide, or they can be administered at separate times. Exemplary TGFβ family members include, by way of example, TGFβ-1, TGFβ-3, BMP2, BMP4, BMP6, and BMP7. Preferred TGFβ polypeptides are encoded by nucleic acids comprising an amino acid sequence at least 60% identical, more preferably 70% identical, and most preferably 80% identical with a vertebrate TGFβ polypeptide, or bioactive fragement thereof. Nucleic acids which encode polypeptides at least about 90%, more preferably at least about 95%, and most preferably at least about 98–99% identical with a vertebrate TGFβ polypeptide, or bioactive fragment thereof, are also within the scope of the invention.

Polypeptides for use in the subject methods include a hedgehog polypeptide comprising at least a bioactive extracellular portion of a hedgehog protein, e.g., the hedgehog polypeptide includes at least 50, 100 or 150 contiguous amino acid residues of an N-terminal half of a hedgehog protein. In preferred embodiments, the hedgehog portion includes at least a portion of the hedgehog protein corresponding to a 19 kd fragment of the extracellular domain of a hedgehog protein (e.g,. the mature N-terminal hedgehog polypeptide).

In preferred embodiments, the hedgehog polypeptide has an amino acid sequence at least 60, 75, 80, 85, 90, 95, 98, 99 or even 100% identical to any of SEQ ID Nos. 10–18. The hedgehog polypeptide can be encoded by a nucleic acid which hybridizes under stringent conditions to a nucleic acid sequence of any of SEQ ID Nos. 1–9.

In another preferred embodiment, the hedgehog polypeptide has an amino acid sequence at least 60, 75, 80, 85, 90, 95, 98, 99 or even 100% identical with all or a portion of a mature hedgehog polypeptide. Exemplary mature hedgehog polypeptides are provided in SEQ ID NO: 20–27. By "a portion of" a mature hedgehog polypeptide is meant at least 50, 100, or 150 contiguous amino acids residues of a mature hedgehog polypeptide.

Hedgehog polypeptides preferred by the present invention, in addition to native hedgehog proteins, comprise an amino acid sequence at least 60%, 70%, 75%, 80%, 85%, 90%, 95%, 98%, 99% or even 100% identical to an amino acid sequence represented in any of SEQ ID Nos: 10–19. In addition, the invention contemplates that hedgehog polypeptides comprising bioactive fragments of at least 50, 100, 150, or greater than 150 contiguous amino acid residues of the N-terminal half of any of SEQ ID NOs: 10–19 are useful in the methods of the present invention.

It is well appreciated in the art that the full length hedgehog protein is processed to yield the mature N-terminal protein which mediates hedgehog signal transduction. The present invention contemplates the use of hedgehog polypeptides comprising an amino acid sequence at least 60%, 70%, 75%, 80%, 85%, 90%, 95%, 98%, 99%, or even 100% identical to any of SEQ ID NOs: 20–27.

In one embodiment, the hedgehog therapeutic is a polypeptide encodable by a nucleotide sequence that hybridizes under stringent conditions to a hedgehog coding sequence represented in one or more of SEQ ID Nos: 1–9. Appropriate stringency conditions which promote nucleic acid hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

As described in the literature, genes for other hedgehog proteins, e.g., from other animals, can be obtained from mRNA or genomic DNA samples using techniques well known in the art. For example, a cDNA encoding a hedgehog protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding a hedgehog protein can also be cloned using established polymerase chain reaction techniques.

Homologs of naturally occurring hedgehog proteins can be generated by mutagenesis, such as by discrete point mutation(s), or by truncation. For instance, mutation can give rise to homologs which retain substantially the same, or merely a subset, of the biological activity of the hedgehog polypeptide from which it was derived. Alternatively, antagonistic forms of the protein can be generated which are able to inhibit the function of the naturally occurring form of the protein, such as by competitively binding to an hedgehog receptor.

Preferred nucleic acids encode a hedgehog polypeptide comprising an amino acid sequence at least 60%, 70%, 75%, 80%, 85%, 90%, 95%, 98%, 99%, or even 100% identical to an amino acid sequence selected from the group consisting of SEQ ID Nos: 10–27.

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence. Further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to an proteolytic N-terminal portion of the mature protein. In addition to proteolytic fragmentation, the vertebrate hedgehog proteins can also be modified post-translationally, such as by glycosylation and/or addition of cholesterol or other lipophilic moiety. Bioactive fragments of hedgehog polypeptides of the present invention have been generated and are described in great detail in, e.g., PCT publications WO 95/18856 and WO 96/17924, hereby incorporated by reference.

The method of the present invention can also be carried out using variant forms of the naturally occurring hedgehog polypeptides, e.g., mutational variants.

As is known in the art, hedgehog polypeptides can be produced by standard biological techniques. For example, a host cell transfected with a nucleic acid vector directing expression of a nucleotide sequence encoding the subject polypeptides can be cultured under appropriate conditions to allow expression of the peptide to occur. The polypeptide hedgehog may be secreted and isolated from a mixture of cells and medium containing the recombinant hedgehog polypeptide. Alternatively, the peptide may be retained cytoplasmically by removing the signal peptide sequence from the recombinant hedgehog gene and the cells harvested, lysed and the protein isolated. A cell culture includes host cells, media and other byproducts. Suitable media for cell culture are well known in the art. The recombinant hedgehog polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant hedgehog polypeptide is a fusion protein containing a domain which facilitates its purification, such as an hedgehog/GST fusion protein. The host cell may be any prokaryotic or eukaryotic cell.

Recombinant hedgehog genes can be produced by ligating nucleic acid encoding an hedgehog protein, or a portion thereof, into a vector suitable for expression in either prokaryotic cells, eukaryotic cells, or both. Expression vectors for production of recombinant forms of the subject hedgehog polypeptides include plasmids and other vectors. For instance, suitable vectors for the expression of a hedgehog polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, an hedgehog polypeptide is produced recombinantly utilizing an expression vector generated by sub-cloning the coding sequence of one of the hedgehog genes represented in SEQ ID Nos: 1–9.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant hedgehog polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of an hedgehog protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing hedgehog-derived polypeptides in a host which produces MAP (e.g., E. coli or CM89 or S. cerevisiae), or in vitro by use of purified MAP (e.g., procedure of Miller et al., supra).

Alternatively, the coding sequences for the polypeptide can be incorporated as a part of a fusion gene including a nucleotide sequence encoding a different polypeptide. It is widely appreciated that fusion proteins can also facilitate the expression of proteins, and accordingly, can be used in the expression of the hedgehog polypeptides of the present invention. For example, hedgehog polypeptides can be generated as glutathione-S-transferase (GST-fusion) proteins. Such GST-fusion proteins can enable easy purification of the hedgehog polypeptide, as for example by the use of glutathione-derivatized matrices (see, for example, Current Protocols in Molecular Biology, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the hedgehog protein (e.g. of the pro-form, in order to permit purification of the poly(His)-hedgehog protein by affinity chromatography using a $Ni^{2+}$ metal resin. The purification leader sequence can then be subsequently removed by treatment with enterokinase (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

Hedgehog polypeptides may also be chemically modified to create hedgehog derivatives by forming covalent or aggregate conjugates with other chemical moieties, such as glycosyl groups, cholesterol, isoprenoids, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

In preferred embodiment, the hedgehog polypeptide is isolated from, or is otherwise substantially free of, other cellular proteins, especially other extracellular or cell surface associated proteins which may normally be associated with the hedgehog polypeptide. The term "substantially free of other cellular or extracellular proteins" (also referred to herein as "contaminating proteins") or "substantially pure or purified preparations" are defined as encompassing preparations of hedgehog polypeptides having less than 20% (by dry weight) contaminating protein, and preferably having less than 5% contaminating protein. By "purified", it is meant that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water and buffers can be present). The term "pure" as used herein preferably has the same numerical limits as "purified" immediately above.

As described above for recombinant polypeptides, isolated hedgehog polypeptides can include all or a portion of the amino acid sequences represented in any of SEQ ID Nos:10–18 or 19. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

With respect to bioactive fragments of hedgehog polypeptide, preferred hedgehog therapeutics include at least 50 contiguous amino acid residues of a hedgehog polypeptide, more preferably at least 100, and even more preferably at least 150 contiguous amino acid residues.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 27–200 of SEQ ID NO: 10, residues 23–198 of SEQ ID NO: 11, residues 28–202 of SEQ ID NO: 12, residues 25–198 of SEQ ID NO: 13, residues 24–197 of SEQ ID NO: 14, residues 24–197 of SEQ ID No. 15, residues 28–202 of SEQ ID No. 16, and residues 23–198 of SEQ ID No. 17. By "corresponding approximately" it is meant that the sequence of interest is at most 20 amino acid residues different in length to the reference sequence, though more preferably at most 5, 10 or 15 amino acid different in length.

The invention further contemplates the use of isolated peptidyl portions of hedgehog proteins. Isolated peptidyl portions can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a hedgehog polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") hedgehog protein. For example, Román et al. (1994) *Eur J Biochem* 222:65–73 describe the use of competitive-binding assays using short, overlapping synthetic peptides from larger proteins to identify binding domains.

The recombinant hedgehog polypeptides of the present invention also include homologs of the authentic hedgehog proteins, such as versions of those protein which are resistant to proteolytic cleavage, as for example, due to mutations which alter potential cleavage sequences or which inactivate an enzymatic activity associated with the protein. Hedgehog homologs of the present invention also include proteins which have been post-translationally modified in a manner different than the authentic protein. Exemplary derivatives of hedgehog proteins include polypeptides which lack N-glycosylation sites (e.g. to produce an unglycosylated protein), which lack sites for cholesterolization, and/or which lack N-terminal and/or C-terminal sequences.

Modification of the structure of the subject hedgehog polypeptides can also be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the hedgehog polypeptides described in more detail herein. Such modified peptides can be produced, for instance, by amino acid substitution, deletion, or addition.

It is well known in the art that one can reasonably expect that certain isolated replacements of amino acids, e.g., replacement of an amino acid residue with another related amino acid (i.e. isosteric and/or isoelectric mutations), can be carried out without major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur containing=cysteine and methionine. (see, for example, *Biochemistry*, 2nd ed., Ed. by L. Stryer, W H Freeman and Co.: 1981). Whether a change in the amino acid sequence of a peptide results in a functional hedgehog homolog (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

It is specifically contemplated that the methods of the present invention can be carried using variants of naturally occurring hedgehog proteins. In one embodiment, the invention contemplates using hedgehog polypeptides generated by combinatorial mutagenesis. Such methods, as are known in the art, are convenient for generating both point and truncation mutants, and can be especially useful for identifying potential variant sequences (e.g. homologs) that are functional in binding to a receptor for hedgehog proteins. The purpose of screening such combinatorial libraries is to generate, for example, novel hedgehog homologs which can act as either agonists or antagonist. To illustrate, hedgehog homologs can be engineered by the present method to provide more efficient binding to a cognate receptor, such as patched, yet still retain at least a portion of an activity associated with hedgehog. Thus, combinatorially-derived homologs can be generated to have an increased potency relative to a naturally occurring form of the protein. Likewise, hedgehog homologs can be generated by the present combinatorial approach to act as antagonists, in that they are able to mimic, for example, binding to other extracellular matrix components (such as receptors), yet not induce any biological response, thereby inhibiting the action of authentic hedgehog or hedgehog agonists. Moreover, manipulation of certain domains of hedgehog by the present method can provide domains more suitable for use in fusion proteins, such as one that incorporates portions of other proteins which are derived from the extracellular matrix and/or which bind extracellular matrix components.

To further illustrate the state of the art of combinatorial mutagenesis, it is noted that the review article of Gallop et al. (1994) *J Med Chem* 37:1233 describes the general state of the art of combinatorial libraries as of the earlier 1990's. In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of hedgehog variants which can be rapidly screened to identify variants/fragments which retained a particular activity of the hedgehog polypeptides. These techniques are exemplary of the art and demonstrate that large libraries of related variants/truncants can be generated and assayed to isolate particular variants without undue experimentation. Gustin et al. (1993) *Virology* 193:653, and Bass et al. (1990) *Proteins: Structure, Function and Genetics* 8:309–314 also describe other exemplary techniques from the art which can be adapted as means for generating mutagenic variants of hedgehog polypeptides.

Indeed, it is plain from the combinatorial mutagenesis art that large scale mutagenesis of hedgehog proteins, without any preconceived ideas of which residues were critical to the biological function, and generate wide arrays of variants having equivalent biological activity. Indeed, it is the ability of combinatorial techniques to screen billions of different variants by high throughout analysis that removes any requirement of a priori understanding or knowledge of critical residues.

To illustrate, the amino acid sequences for a population of hedgehog homologs or other related proteins are aligned, preferably to promote the highest homology possible. Such a population of variants can include, for example, hedgehog homologs from one or more species. Amino acids which appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g. for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, SA (1983) *Tetrahedron* 39:3; Itakura et al. (1981) *Recombinant DNA,* *Proc 3rd Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature,* 2., In Maenner and Manderick, eds., Elsevier Publishing Co., Amsterdam, pp. 401–410; Delgrave et al., 1993, *Protein Engineering* 6(3):327–331).

Subsequent testing of the hedgehog analogs, e.g., to discern between agonists and antagonists can be carried using any of a wide range of bioassays known in the art.

Recombinantly produced forms of the hedgehog proteins can be produced using, e.g, expression vectors containing a nucleic acid encoding a hedgehog polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a hedgehog polypeptide. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a nucleic acid sequence when operatively linked to it, may be used in these vectors to express nucleic acid sequences encoding hedgehog polypeptide. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

In addition to providing a ready source of hedgehog polypeptides for purification, the gene constructs of the present invention can also be used as a part of a gene therapy protocol to deliver nucleic acids encoding either an agonistic or antagonistic form of a hedgehog polypeptide. Thus, another aspect of the invention features expression vectors for in vivo or in vitro transfection of a hedgehog polypeptide in particular cell types so as cause ectopic expression of a hedgehog polypeptide.

Formulations of such expression constructs may be administered in any biologically effective carrier, e.g. any formulation or composition capable of effectively delivering the recombinant gene to cells in vivo. Approaches include insertion of the hedgehog coding sequence in viral vectors including recombinant retroviruses, adenovirus, adeno-associated virus, and herpes simplex virus-l, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of hedgehog expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the hedgehog polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host.

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a hedgehog polypeptide and renders the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the hedgehog gene of the retroviral vector.

Another viral gene delivery system useful in the present method utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N. J., 1991) vol. 7. pp. 109–127). Expression of the inserted hedgehog gene can be under control of, for example, the E1A promoter, the major late promoter (MLP) and associated leader sequences, the E3 promoter, or exogenously added promoter sequences.

In addition to viral transfer methods, such as those illustrated above, non-viral methods can also be employed to cause expression of a hedgehog polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the hedgehog polypeptide gene by the targeted cell. Exemplary gene delivery systems of this type include liposomal derived systems, poly-lysine conjugates, and artificial viral envelopes.

In clinical settings, the gene delivery systems for the therapeutic hedgehog gene can be introduced into a patient by any of a number of methods, each of which is familiar in the art. For instance, a pharmaceutical preparation of the gene delivery system can be introduced, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof.

III. Exemplary Applications of Method and Compositions

The present invention makes available effective therapeutic methods and compositions for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. It may prevent the onset or exacerbation of degenerative disease if applied early enough after trauma.

In an illustrative embodiment, the subject method is used to treat cartilage of a diarthroidal joint, such as knee, an ankle, an elbow, a hip, a wrist, a knuckle of either a finger or toe, or a temperomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. An injection of a pharmeceutical preparation of a three dimensional cartilage matrix into the joint with, for instance, an arthroscopic needle, can be used to treat the afflicted cartilage. In some instances, the three dimensional cartilage matrix is transplanted directly to the site of cartilage damage or injury.

Moreover, as described above, the compound can be formulated and delivered to a specific location. For instance, slow release polymers can be localized to a particular treatment area of a mensical disc. To illustrate, degenerative changes are prominent in the triangular cartilage disc of the wrist joint of elderly people. The degeneration is more frequent and advanced on the ulnar side of the disc, perhaps because the biomechanical forces are more intense on that side. The degeneration affects the avascular portions of the disc but not the vascularized edges. Thus, a compound can be localized to the center of the ulnar face of the disc to enhance reparative process in that portion of the disc without substantially altering the integrity of the rest of the disc.

In another illustrated embodiment, the subject method can be used to treat cartilage of the costal sternum. After open chest surgery, such treatment can be opportunely employed in speeding reattachment of severed ribs to the sternum, as well as to decrease the amount of fibrotic tissue generated during healing.

In yet another embodiment of the subject method, a subject compound is contacted with cartilage of the pubic symphysis to enhance reattachment of the hip bones. For example, such treatments can be utilized in a female patient after delivery of a baby in order to mediate healing of the pubic symphysis which has undergone an intracartilaginous fissure from the degeneration of hyaline cartilage before and during labor.

In still a further embodiment, the subject method is applied to prevent replacement of hyaline cartilage after injury or other degenerative disorders, by other kinds of connective tissue such as fibroses or fibrous cartilage, as well as to prevent ossification of cartilaginous tissues. For example, the present invention can be used in the treatment of disorders in which cartilage is replaced by bone. Treatment of this tissue by the subject method can inhibit the spread of mineralisation into the cartilage tissue by stimulating production of new cartilage matrix which turns over or otherwise replaces cartilage which is undergoing osteogenic processes.

The present invention further contemplates the use of the subject method in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs because implanted tissue, which has not differentiated under those conditions, lacks the ability to appropriately respond. For instance, when meniscal cartilage is used to repair anterior cruciate ligaments, the tissue undergoes a metaplasia to pure fibrous tissue.

By promoting chondrocyte growth and/or proliferation, the present invention can be used to address this problem by causing the implanted cells to become more adaptive to the new environment and effectively resemble hypertrophic chondrocytes of an earlier developmental stage of the tissue. Thus, the action of chondrogenesis in the implanted tissue, as provided by the subject method, and the mechanical forces on the actively remodeling tissue will synergize to produce an improved implant more suitable for the new function to which it is to be put.

In similar fashion, the subject method can be applied to enhance remodeling of ligaments or tendons that are surgically shortened. For example, the present invention can be used to treat temperomandibular joint dysfunction (TMJ) either in regenerating the disc (as described for other joints above) or in the repair or replacement of the ligamental tissue which articulates the disc with the surrounding skeletal bones to correctly position the disc on the head of the condyle. For instance, in certain forms of TMJ, the ligaments have been stretched such that the interarticular disc is positioned either anterior or posterior to the condyle head. Surgical procedures to shorten the ligaments have been used to correct this deformity. The subject method can be used in the treatment of the shortened ligament to provide an improved ligament having zonal patterning that has advantageously been developed by the active remodeling of the "new" ligament by chondrocyte activation. Moreover, the present invention can prevent the occurrence of fibrotic tissue in the shortened ligament.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) Clin Orthop Relat Red 252:129), isolated chondrocytes (Grande et al. (1989) J Orthop Res 7:208; and Takigawa et al. (1987) Bone Miner 2:449), and chondrocytes attached to natural or synthetic polymers (Walitani et al. (1989) J Bone Jt Surg 71B:74; Vacanti et al. (1991) Plast Reconstr Surg 88:753; von Schroeder et al. (1991) J Biomed Mater Res 25:329; Freed et al. (1993) J Biomed Mater Res 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as a function of hydrolysis of the polymer backbone into innocuous monomers. The scaffolds are designed to allow adequate nutrient and gas exchange to the cells until engraftment occurs. The cells can be cultured in vitro until adequate cell volume and density have developed for the cells to be implanted. One advantage of the scaffolds is that they can be cast or molded into a desired shape on an individual basis, so that the final product closely resembles the patient's own ear or nose (by way of example), or flexible scaffolds can be used which allow for manipulation at the time of implantation, as in a joint.

In another aspect, the present invention provides pharmaceutical preparations comprising the three dimensional cartilage matrices of the present invention. The three dimensional cartilage matrices for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the subject compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the subject compounds suitable for veterinary uses, e.g., for the treatment of livestock or domestic animals, e.g., dogs.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant at a particular target site.

The preparations of the present invention are of course given by forms suitable for each administration route. For example, they are administered in tablets or capsule form, by injection, inhalation, eye lotion, ointment, suppository, controlled release patch, administration by injection, infusion or inhalation; topically by lotion or ointment; and rectally by suppositories. Oral and topical administrations are preferred.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and thus, is subject to metabolism and other like processes.

These compounds may be administered to humans and other animals for therapy by any suitable route of administration, including orally, nasally, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon factors including the patient's age, sex, and the severity of their injury or disease.

The term "treatment" is intended to encompass also prophylaxis, therapy and cure.

The patient receiving this treatment is any animal in need, including primates, in particular humans, and other mammals such as equines, cattle, swine and sheep; as well as poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Exemplification

The invention now being generally described, it will be more readily understood by reference to the following examples which are included merely for purposes of illustration of certain aspects and embodiments of the present invention, and are not intended to limit the invention.

Example 1

Isolation of Human Mesenchymal Stem Cells

Mesenchymal stem cells were derived from human volunteers under general anesthesia. Bone marrow was harvested from the iliac crest by aspiration. Approximately 5 mL of bone marrow was suspended in essential medium containing 20% fetal bovine serum (FBS), antibiotics, and glutamine (Sigma). Under these conditions, mesenchymal stem cells adhere to the culture flask while hematopoietic stem cells do not adhere. The non-adherent cells, as well as any debris, is easily separated from the adherent mesenchymal stem cells.

Mesenchymal stem cells were plated at a density of $1 \times 10^6$/mL in a six well plate. Following adhesion of the cells to the plate, cells were treated with either medium containing 20% FBS, with medium supplemented with TGFβ-1, or with medium supplemented with sonic hedgehog.

Example 2

Change in Mesenchymal Stem Cell Behavior Following Factor Treatment

Following adhesion of cells to the plate, cells were treated with either medium containing 20% FBS (negative control), medium containing 1 ng/mL TGFβ-1, or medium containing 100 ng/mL of the lipid modified N-terminal fragment of sonic hedgehog. In all cases, the medium was changes twice per week throughout the duration of the experiment.

Cells treated with 20% FBS attached and proliferated in culture. Within three weeks, the cells proliferated to form a monolayer of stromal cells over the entire culture well. No areas of differentiation were observed in the well.

Cells treated with TGFβ-1 appeared morphologically distinct after a week in culture. The cells appeared larger, and later molecular characterization of these cells revealed a correlation between this change in cell size and matrix production (data not shown).

Cells treated with sonic hedgehog proliferated efficiently during the first two weeks in culture. Following this period of active proliferation, the cells appeared to migrate and clustered in one half the area of the culture well. This clustering was extensive, and left half of the culture well free of cells. After approximately three weeks in culture, the cluster of cells formed a grayish-white ball which was only loosely adherent and easily detached from the surrounding well (FIG. 1).

Example 3

Molecular Characterization of Cell Behavior Following Factor Treatment

Mesenchymal stem cell cultures were established, as described in detail above. Cells were cultured in the presence of 20% FBS, 1 ng/mL TGFβ-1, or 100 ng/mL lipid modified sonic hedgehog, and the medium was changed twice per week. After 21 days in culture, tissue was harvested, and fixed overnight in formaline solution. Fixed tissue was washed, dehydrated, embedded in paraffin, and 4 µm sections were cut using a microtome. Sections were mounted on adhesive slides, and processed for histology and immunohistochemistry.

a. Hematoxyline-Eosine Staining

Figure 2B:

Mounted paraffin sections were stained with hematoxyline-eosine, and viewed under a light microscope. FIG. 2 shows that tissue harvested following 21 days of treatment with sonic hedgehog is highly organized, contains several folded layers, and produces abundant matrix.

b. Alcian Blue staining

Mounted paraffin sections were stained with Alcian blue. Sections were treated with Alcian blue, pH 2.5 and 3% Acetic acid for five minutes. Following treatment, the sections were washed with ultrapure water.

Figure 3:
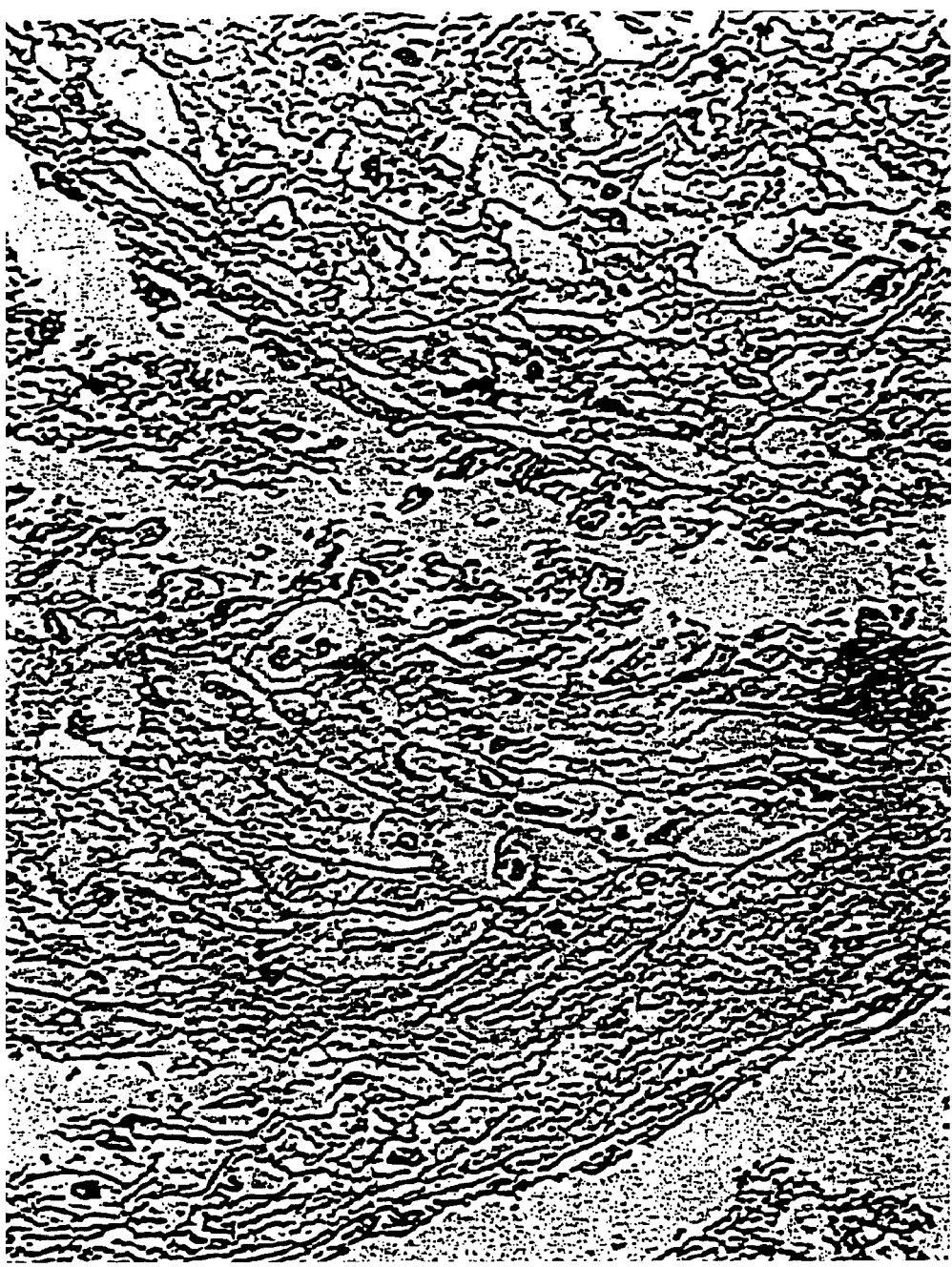
FIG. 3 shows Alcian blue and Fast red staining of paraffin sections of tissue treated with sonic hedgehog and harvested after 21 days.

Positive Alcian blue staining reveals that the three dimensional cartilage matrix contains acid mucopolysaccharids (FIG. 3). Although indicative of a cartilage matrix, this does not appear to be a completely mature matrix. This may be due to the duration of the culture, or the concentrations of sonic hedgehog protein used in the experiment.

c. Immunohistochemistry

Mounted paraffin sections were processed for immunohistochemistry with an automatic stainer (DAKO TechMate™) using indirect streptavidin-biotin methods with a Fuchsintype chromogen. The following primary antibodies were used: vimentin, collagen II, Indian hedgehog, PTHrp, BMPR-IA, BMPR-IB, and BMPR-II. Immunohistochemistry was by standard methods except for the PTHrp antibody which required incubation of the tissue with proteinase K.

Figure 4:
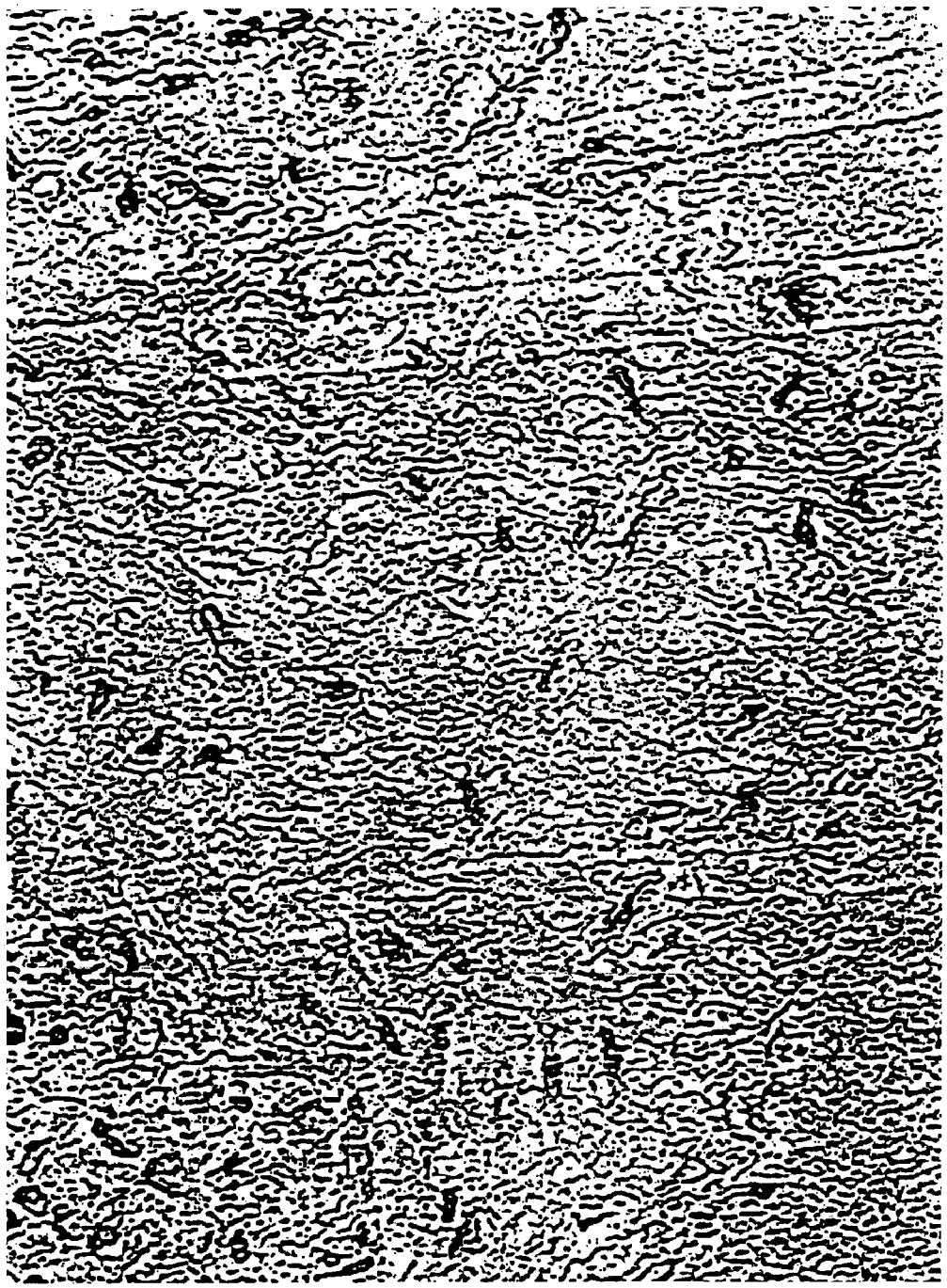
FIG. 4 shows immunohistochemical analysis of BMPR-IA expression on paraffin sections of tissue treated with sonic hedgehog and harvested after 21 days. Note that expression of BMPR-IA protein is not detected using this method.
Figure 5A:
FIGS. 5A–5B show immunohistochemical analysis of Collagen Type II expression on paraffin sections of tissue treated with sonic hedgehog and harvested after 21 days. Note that Collagen Type II protein is strongly expressed, and can be observed at low (A) and high (B) power.
Figure 5B:

The results of immunohistochemical analysis of mesenchymal stem cells following 21 days of treatment with sonic hedgehog is summarized in FIG. 6. The tissue was strongly immunopositive for vimentin and collagen II (FIG. 5), and immunopositive for PTHrp, BMPR-IB, and BMPR-II. However, the tissue was immunonegative for Indian hedgehog and BMPR-IA (FIG. 4). These results indicate the cartilaginous character of the three dimensional matrix formed following treatment of mesenchymal stem cells with sonic hedgehog.

Furthermore, the induction of several BMP receptors in this tissue, as well as the robust proliferative effects observed following treatment of mesenchymal stem cells with TGFβ-1, suggest that treatment of cells with both hedgehog, or an agent that stimulate hedgehog signaling, and a TGFβ family member may also augment the formation of three dimensional cartilage matrices.

All publications, patents and patent applications are herein incorporated by reference in their entirety to the same extent as if each individual publication, patent or patent application was specifically and individually indicated to be incorporated by reference in its entirety.

Equivalents

Those skilled in the art will recognize, or be able to ascertain using no more than routine experimentation, many equivalents to the specific embodiments of the invention described herein. Such equivalents are intended to be encompassed by the following claims.

TABLE 1

|  | nucleic acid sequence | amino acid sequence |
| --- | --- | --- |
| Chicken Sonic hedgehog | SEQ ID NO: 1 | SEQ ID NO: 10 |
| Mouse Desert hedgehog | SEQ ID NO: 2 | SEQ ID NO: 11 |
| Mouse Indian hedgehog | SEQ ID NO: 3 | SEQ ID NO: 12 |
| Mouse Sonic hedgehog | SEQ ID NO: 4 | SEQ ID NO: 13 |
| Zebrafish Sonic hedgehog | SEQ ID NO: 5 | SEQ ID NO: 14 |
| Human Sonic hedgehog | SEQ ID NO: 6 | SEQ ID NO: 15 |
| Human Indian hedgehog | SEQ ID NO: 7 | SEQ ID NO: 16 |
| Human Desert hedgehog | SEQ ID NO: 8 | SEQ ID NO: 17 |
| Drosophila hedgehog | SEQ ID NO: 9 | SEQ ID NO: 18 |
| Hedgehog consensus | XXXXXXXXXXXXX | SEQ ID NO: 19 |
| Chicken Sonic hedgehog (mature) | XXXXXXXXXXXXX | SEQ ID NO: 20 |
| Mouse Desert hedgehog (mature) | XXXXXXXXXXXXX | SEQ ID NO: 21 |
| Mouse Indian hedgehog (mature) | XXXXXXXXXXXXX | SEQ ID NO: 22 |
| Mouse Sonic hedgehog (mature) | XXXXXXXXXXXXX | SEQ ID NO: 23 |
| Zebrafish Sonic hedgehog (mature) | XXXXXXXXXXXXX | SEQ ID NO: 24 |
| Human Sonic hedgehog (mature) | XXXXXXXXXXXXX | SEQ ID NO: 25 |
| Human Indian hedgehog (mature) | XXXXXXXXXXXXX | SEQ ID NO: 26 |
| Human Desert hedgehog (mature) | XXXXXXXXXXXXX | SEQ ID NO: 27 |

I claim:

1. An in vitro method for promoting the formation of a three dimensional cartilage matrix, comprising
   contacting adult mesenchymal stem cells with a composition comprising a sonic hedgehog polypeptide comprising an amino acid sequence at least 95% identical to one or more of SEQ ID NO: 20, SEQ ID NO: 23, SEQ ID NO: 24, or SEQ ID NO: 25, which sonic hedgehog polypeptide is modified with a lipid moiety and binds to patched and promotes hedgehog signaling,
   wherein contacting said cells with said composition promotes formation of said three dimensional cartilage matrix from said adult mesenchymal stem cells.

2. An in vitro method for promoting the formation of a three dimensional cartilage matrix, comprising
   contacting adult mesenchymal stem cells with a composition comprising a sonic hedgehog polypeptide and a TGFβ-1 polypeptide, which sonic hedgehog polypeptide comprises an amino acid sequence at least 95% identical to one or more of SEQ ID NO: 20, SEQ ID NO: 23, SEQ ID NO: 24, or SEQ ID NO: 25, and which sonic hedgehog polypeptide is modified with a lipid moiety and binds to patched and promotes hedgehog signaling,
   wherein contacting said cells with said composition promotes formation of said three dimensional cartilage matrix from said adult mesenchymal stem cells.

3. An in vitro method for promoting cell migration, proliferation, and differentiation of adult mesenchymal stem cells, thereby resulting in the formation of a three dimensional cartilage matrix, comprising
   contacting adult mesenchymal stem cells with a composition comprising a sonic hedgehog polypeptide comprising an amino acid sequence at least 95% identical to one or more of SEQ ID NO: 20, SEQ ID NO: 23, SEQ ID NO: 24, or SEQ ID NO: 25, which sonic hedgehog polypeptide is modified with a lipid moiety and binds to patched and promotes hedgehog signaling,
   wherein contacting said cells with said composition promotes cell migration, proliferation, and differentiation of said adult mesenchymal stem cells, thereby resulting in formation of said three dimensional cartilage matrix from said adult mesenchymal stem cells.

4. An in vitro method for promoting cell migration, proliferation, and differentiation of adult mesenchymal stem cells, thereby resulting in the formation of a three dimensional cartilage matrix, comprising
   contacting adult mesenchymal stem cells with a composition comprising a sonic hedgehog polypeptide and a TGFβ-1 polypeptide, which sonic hedgehog polypeptide comprises an amino acid sequence at least 95% identical to one or more of SEQ ID NO: 20, SEQ ID NO: 23, SEQ ID NO: 24, or SEQ ID NO: 25, and which sonic hedgehog polypeptide is modified with a lipid moiety and binds to patched and promotes hedgehog signaling,
   wherein contacting said cells with said composition promotes cell migration, proliferation, and differentiation of said adult mesenchymal stem cells, thereby resulting in formation of said three dimensional cartilage matrix from said adult mesenchymal stem cells.

5. The method of any of claims 1, 2, 3, or 4, wherein the mesenchymal stem cells are derived from a mammal.

6. The method of claim 5, wherein the cells are derived from a human.

7. The method of at least one of claims 2 or 4, wherein the hedgehog polypeptide and the TGFβ-1 polypeptide are co-administered.

8. The method of at least one of claims 2 or 4, wherein the hedgehog polypeptide and the TGFβ-1 polypeptide are administered at different times.

9. The method of any of claims 1, 2, 3, or 4, wherein the three dimensional cartilage matrix includes Alcian Blue positive cells.

10. The method of any of claims 1, 2, 3, or 4, wherein the three dimensional cartilage matrix includes vimentin and collagen II immunopositive cells.

11. The method of any of claims 1, 2, 3, or 4, wherein the three dimensional cartilage matrix includes PTHrp, BMPR-IB, and BMPR-II immunopositive cells.

12. The method of claim 10, wherein the three dimensional cartilage matrix does not include Indian hedgehog or BMPR-IA immunopositive cells.

13. The method of claim 11, wherein the three dimensional cartilage matrix does not include Indian hedgehog or BMPR-IA immunopositive cells.

14. The method of any of claims 1, 2, 3, or 4, wherein the adult mesenchymal stem cells are human adult mesenchymal stem cells.

15. A method for producing a three dimensional cartilage matrix, comprising
   (a) establishing a culture comprising adult mesenchymal stem cells; and
   (b) contacting the culture comprising adult mesenchymal stem cells with an amount of a lipid modified sonic hedgehog polypeptide sufficient to promote the growth and differentiation of the adult mesenchymal stem cells, thereby producing the three dimensional cartilage matrix in the culture of cells,
   wherein the sonic hedgehog polypeptide comprises an amino acid sequence at least 95% identical to one or more of SEQ ID NO: 20, SEQ ID NO: 23, SEQ ID NO: 24, or SEQ ID NO: 25.

16. A method for producing a three dimensional cartilage matrix, comprising
   (a) establishing a culture comprising adult mesenchymal stem cells; and
   (b) contacting the culture comprising adult mesenchymal stem cells with an amount of a lipid modified sonic hedgehog polypeptide and a TGFβ-1 polypeptide sufficient to promote the growth and differentiation of the adult mesenchymal stem cells, thereby producing the three dimensional cartilage matrix in the culture of cells,
   wherein the sonic hedgehog polypeptide comprises an amino acid sequence at least 95% identical to one or more of SEQ ID NO: 20, SEQ ID NO: 23, SEQ ID NO: 24, or SEQ ID NO: 25.

17. The method of claim 15 or 16, further comprising
   (c) isolating the three dimensional cartilage matrix from the culture comprising adult mesenchymal stem cells.

18. The method of claim 15 or 16, further comprising
   (c) providing a scaffold to influence the shape of the three dimensional cartilage matrix; and
   (d) isolating the three dimensional cartilage matrix from the culture comprising adult mesenchymal stem cells.

19. The method of claim 15 or 16, wherein the adult mesenchymal stem cells are human adult mesenchymal stem cells.

20. The method of claim 15 or 16, wherein the three dimensional cartilage matrix includes Alcian Blue positive cells.

21. The method of claim 15 or 16, wherein the three dimensional cartilage matrix includes vimentin and collagen II immunopositive cells.

22. The method of claim 15 or 16, wherein the three dimensional cartilage matrix includes PTHrp, BMPR-IB, and BMPR-II immunopositive cells.

23. The method of claim 21, wherein the three dimensional cartilage matrix does not include Indian hedgehog or BMPR-IA immunopositive cells.

24. The method of claim 22, wherein the three dimensional cartilage matrix does not include Indian hedgehog or BMPR-IA immunopositive cells.

* * * * *

SEQUENCE LISTING

```
<160> NUMBER OF SEQ ID NOS: 27

<210> SEQ ID NO 1
<211> LENGTH: 1277
<212> TYPE: DNA
<213> ORGANISM: Gallus gallus

<400> SEQUENCE: 1
atggtcgaaa tgctgctgtt gacaagaatt ctcttggtgg gcttcatctg cgctcttta      60 gtctcctctg ggctgacttg tggaccaggc aggggcattg gaaaaaggag gcaccccaaa    120
aagctgaccc cgttagccta taagcagttt attcccaatg tggcagagaa gacgctaggg    180
```

```
gccagtggaa gatatgaagg gaagatcaca agaaactccg agagatttaa agaactaacc      240
ccaaattaca accctgacat tatttttaag gatgaagaga acacgggagc tgacagactg      300
atgactcagc gctgcaagga caagctgaat gccctggcga tctcggtgat gaaccagtgg      360
cccggggtga agctgcgggt gaccgagggc tgggacgagg atggccatca ctccgaggaa      420
tcgctgcact acgagggtcg cgccgtggac atcaccacgt cggatcggga ccgcagcaag      480
tacggaatgc tgcccgcct cgccgtcgag gccggcttcg actgggtcta ctacgagtcc       540
aaggcgcaca tccactgctc cgtcaaagca gaaaactcag tggcagcgaa atcaggaggc      600
tgcttccctg gctcagccac agtgcacctg agcatggag gcaccaagct ggtgaaggac       660
ctgagccctg ggaccgcgt gctggctgct gacgcggacg gccggctgct ctacagtgac       720
ttcctcacct tcctcgaccg gatggacagc tcccgaaagc tcttctacgt catcgagacg      780
cggcagcccc gggcccggct gctactgacg gcggcccacc tgctctttgt ggccccccag      840
cacaaccagt cggaggccac aggtccacc agtggccagg cgctcttcgc cagcaacgtg       900
aagcctggcc aacgtgtcta tgtgctgggc gagggcgggc agcagctgct gccggcgtct      960
gtccacagcg tctcattgcg ggaggaggcg tccggagcct acgccccact caccgcccag     1020
ggcaccatcc tcatcaaccg ggtgttggcc tcctgctacg ccgtcatcga ggagcacagt     1080
tgggcccatt gggccttcgc accattccgc ttggctcagg gctgctggc cgccctctgc      1140 ccagatgggg ccatccctac tgccgccacc accaccactg gcatccattg gtactcacgg     1200
ctcctctacc gcatcggcag ctgggtgctg gatggtgacg cgctgcatcc gctgggcatg     1260
gtggcaccgg ccagctg                                                   1277

<210> SEQ ID NO 2
<211> LENGTH: 1190
<212> TYPE: DNA
<213> ORGANISM: Mus musculus

<400> SEQUENCE: 2
atggctctgc cggccagtct gttgcccctg tgctgcttgg cactcttggc actatctgcc       60
cagagctgcg ggccgggccg aggaccggtt ggccggcggc gttatgtgcg caagcaactt      120
gtgcctctgc tatacaagca gtttgtgccc agtatgcccg agcggaccct gggcgcgagt      180
gggccagcgg aggggagggt aacaagggg tcggagcgct ccgggacct cgtacccaac       240 tacaaccccg acataatctt caaggatgag gagaacagcg gcgcagaccg cctgatgaca      300
gagcgttgca aagagcgggt gaacgctcta gccatcgcg tgatgaacat gtggcccgga       360
gtacgcctac gtgtgactga aggctgggac gaggacggcc accacgcaca ggattcactc      420
cactacgaag gccgtgcctt ggacatcacc acgtctgacc gtgaccgtaa taagtatggt      480
ttgttggcgc gcctagctgt ggaagccgga ttcgactggg tctactacga gtcccgcaac     540
cacatccacg tatcggtcaa agctgataac tcactggcgg tccgagccgg aggctgcttt     600
ccgggaaatg ccacggtgcg cttgcggagc ggcgaacgga aggggctgag ggaactacat     660
cgtggtgact gggtactggc cgctgatgca gcgggccgag tggtacccac gccagtgctg     720
ctcttcctgg accgggatct gcagcgccgc gcctcgttcg tggctgtgga accgagcgg     780 cctccgcgca aactgttgct cacaccctgg catctggtgt tcgctgctcg cgggccagcg     840
cctgctccag gtgactttgc accggtgttc gcgcgccgct acgtgctgg cgactcggtg     900 ctggctcccg gcggggacgc gctccagccg gcgcgctag cccgcgtggc gcgcgaggaa      960
gccgtgggcg tgttcgcacc gctcactgcg cacgggacgc tgctggtcaa cgacgtcctc    1020
```

```
gcctcctgct acgcggttct agagagtcac cagtgggccc accgcgcctt cgcccctttg   1080
cggctgctgc acgcgctcgg ggctctgctc cctggggggtg cagtccagcc gactggcatg   1140
cattggtact ctcgcctcct ttaccgcttg gccgaggagt taatgggctg              1190
```

<210> SEQ ID NO 3
<211> LENGTH: 1281
<212> TYPE: DNA
<213> ORGANISM: Mus musculus

<400> SEQUENCE: 3

```
atgtctcccg cctggctccg gccccgactg cggttctgtc tgttcctgct gctgctgctt   60
ctggtgccgg cggcgcgggg ctgcgggccg gccgggtgg tgggcagccg ccggaggccg    120
cctcgcaagc tcgtgcctct tgcctacaag cagttcagcc ccaacgtgcc ggagaagacc   180
ctgggcgcca gcgggcgcta cgaaggcaag atcgcgcgca gctctgagcg cttcaaagag   240
ctcaccccca actacaatcc cgacatcatc ttcaaggacg aggagaacac gggtgccgac   300
cgcctcatga cccagcgctg caaggaccgt ctgaactcac tggccatctc tgtcatgaac   360
cagtggcctg gtgtgaaact gcgggtgacc gaaggccggg atgaagatgg ccatcactca   420
gaggagtctt tacactatga gggccgcgcg gtggatatca ccacctcaga ccgtgaccga   480
aataagtatg gactgctggc gcgcttagca gtggaggccg gcttcgactg ggtgtattac   540
gagtccaagg cccacgtgca ttgctctgtc aagtctgagc attcggccgc tgccaagaca   600
ggtggctgct ttcctgccgg agcccaggtg cgcctagaga acggggagcg tgtggccctg   660
tcagctgtaa agccaggaga ccgggtgctg gccatggggg aggatgggac cccaccttc    720 agtgatgtgc ttatttttcct ggaccgcgag ccaaaccggc tgagagcttt ccaggtcatc   780
gagactcagg atcctccgcg tcggctggcg ctcacgcctg cccacctgct cttcattgcg   840
gacaatcata cagaaccagc agcccacttc cgggccacat tgccagcca tgtgcaacca    900 ggccaatatg tgctggtatc aggggtacca ggcctccagc ctgctcgggt ggcagctgtc   960
tccacccacg tggcccttgg gtcctatgct cctctcacaa gcatgggac acttgtggtg    1020 gaggatgtgg tggcctcctg ctttgcagct gtggctgacc accatctggc tcagttggcc   1080
ttctggcccc tgcgactgtt tcccagtttg gcatggggca gctggacccc aagtgagggt   1140
gttcactcct acccctcagat gctctaccgc ctgggcgtc tcttgctaga agagagcacc   1200
ttccatccac tgggcatgtc tggggcagga agctgaaggg actctaacca ctgccctcct   1260
ggaactgctg tgcgtggatc c                                            1281
```

<210> SEQ ID NO 4
<211> LENGTH: 1313
<212> TYPE: DNA
<213> ORGANISM: Mus musculus

<400> SEQUENCE: 4

```
atgctgctgc tgctggccag atgttttctg gtgatccttg cttcctcgct gctggtgtgc   60
cccgggctgg cctgtgggcc cggcaggggg tttggaaaga ggcggcaccc caaaaagctg   120 accccttag cctacaagca gtttattccc aacgtagccg agaagaccct aggggccagc   180
ggcagatatg aagggaagat cacaagaaac tccgaacgat ttaaggaact cacccccaat   240
tacaaccccg acatcatatt taaggatgag gaaaacacgg gagcagaccg gctgatgact   300
cagaggtgca agacaagtt aaatgccttg gccatctctg tgatgaacca gtggcctgga   360
```

```
gtgaggctgc gagtgaccga gggctgggat gaggacggcc atcattcaga ggagtctcta      420
cactatgagg gtcgagcagt ggacatcacc acgtccgacc gggaccgcag caagtacggc      480
atgctggctc gcctggctgt ggaagcaggt ttcgactggg tctactatga atccaaagct      540
cacatccact gttctgtgaa agcagagaac tccgtggcgg ccaaatccgg cggctgtttc      600
ccgggatccg ccaccgtgca cctggagcag ggcggcacca agctggtgaa ggacttacgt      660 cccgagacc gcgtgctggc ggctgacgac cagggccggc tgctgtacag cgacttcctc      720
accttcctgg accgcgacga aggcgccaag aaggtcttct acgtgatcga gacgctggag      780
ccgcgcgagc gcctgctgct caccgccgcg cacctgctct cgtggcgcc gcacaacgac      840 tcggggccca cgcccgggcc aagcgcgctc tttgccagcc gcgtgcgccc gggcagcgc      900 gtgtacgtgg tggctgaacg cggcggggac cgccggctgc tgcccgccgc ggtgcacagc      960
gtgacgctgc gagaggagga ggcgggcgcg tacgcgccgc tcacggcgca cggcaccatt     1020
ctcatcaacc gggtgctcgc ctcgtgctac gctgtcatcg aggagcacag ctgggcacac     1080
cgggccttcg cgcctttccg cctggcgcac gcgctgctgg ccgcgctggc acccgcccgc     1140
acggacggcg ggggcggggg cagcatccct gcagcgcaat ctgcaacgga agcgaggggc     1200
gcggagccga ctgcgggcat ccactggtac tcgcagctgc tctaccacat tggcacctgg     1260
ctgttggaca gcgagaccat gcatcccttg ggaatggcgg tcaagtccag ctg            1313
```

<210> SEQ ID NO 5
<211> LENGTH: 1256
<212> TYPE: DNA
<213> ORGANISM: Danio rerio

<400> SEQUENCE: 5

```
atgcggcttt tgacgagagt gctgctggtg tctcttctca ctctgtcctt ggtggtgtcc       60
ggactggcct gcggtcctgg cagaggctac ggcagaagaa gacatccgaa gaagctgaca      120
cctctcgcct acaagcagtt catacctaat gtcgcggaga agaccttagg ggccagcggc      180
agatacgagg gcaagataac gcgcaattcg gagagattta agaacttac tccaaattac       240 aatcccgaca ttatctttaa ggatgaggag aacacgggag cggacaggct catgacacag      300
agatgcaaag acaagctgaa ctcgctggcc atctctgtaa tgaaccactg gccaggggtt      360
aagctgcgtg tgacagaggg ctgggatgag acggtcacc attttgaaga atcactccac      420
tacgagggaa gagctgttga tattaccacc tctgaccgag acaagagcaa atacgggaca      480
ctgtctcgcc tagctgtgga ggctggattt gactgggtct attacgagtc caaagcccac      540
attcattgct ctgtcaaagc agaaaattcg gttgctgcga atctgggggg ctgtttccca      600
ggttcggctc tggtctcgct ccaggacgga ggacagaagg ccgtgaagga cctgaacccc      660
ggagacaagg tgctggcggc agacagcgcg ggaaacctgg tgttcagcga cttcatcatg      720
ttcacagacc gagactccac gacgcgacgt gtgtttacg tcatagaaac gcaagaaccc      780
gttgaaaaga tcaccctcac cgccgctcac ctccttttg tcctcgacaa ctcaacggaa      840
gatctccaca ccatgaccgc cgcgtatgcc agcagtgtca gagccggaca aaaggtgatg      900
gttgttgatg atagcggtca gcttaaatct gtcatcgtgc agcggatata cacggaggag      960 cagcgggct cgttcgcacc agtgactgca catgggacca ttgtggtcga cagaatactg     1020
gcgtcctgtt acgccgtaat agaggaccag gggcttgcgc atttggcctt cgcgcccgcc     1080
aggctctatt attacgtgtc atcattcctg tcccccaaaa ctccagcagt cggtccaatg     1140
cgactttaca acaggagggg gtccactggt actccaggct cctgtcatca aatgggaacg     1200
```

```
tggcttttgg acagcaacat gcttcatcct ttggggatgt cagtaaactc aagctg        1256

<210> SEQ ID NO 6
<211> LENGTH: 1425
<212> TYPE: DNA
<213> ORGANISM: Homo sapiens
<220> FEATURE:
<221> NAME/KEY: misc_feature
<222> LOCATION: (1387)..(1389)
<223> OTHER INFORMATION: n=a, c, g, or t

<400> SEQUENCE: 6
atgctgctgc tggcgagatg tctgctgcta gtcctcgtct cctcgctgct ggtatgctcg     60
ggactggcgt gcggaccggg caggggttc gggaagagga ggcaccccaa aaagctgacc    120
cctttagcct acaagcagtt tatccccaat gtggccgaga agaccctagg cgccagcgga    180
aggtatgaag ggaagatctc cagaaactcc gagcgattta aggaactcac ccccaattac    240
aaccccgaca tcatatttaa ggatgaagaa acaccggag cggacaggct gatgactcag    300
aggtgtaagg acaagttgaa cgctttggcc atctcggtga tgaaccagtg gccaggagtg    360
aaactgcggg tgaccgaggg ctgggacgaa gatggccacc actcagagga gtctctgcac    420
tacgagggcc gcgcagtgga catcaccacg tctgaccgcg accgcagcaa gtacggcatg    480
ctggcccgcc tggcggtgga ggccggcttc gactgggtgt actacgagtc caaggcacat    540
atccactgct cggtgaaagc agagaactcg gtgcggcca atcgggagg ctgcttcccg    600 ggctcggcca cggtgcacct ggagcagggc ggcaccaagc tggtgaagga cctgagcccc    660
ggggaccgcg tgctggcggc ggacgaccag ggccggctgc tctacagcga cttcctcact    720
ttcctggacc gcgacgacgg cgccaagaag gtcttctacg tgatcgagac gcgggagccg    780
cgcgagcgcc tgctgctcac cgccgcgcac ctgctctttg tggcgccgca caacgactcg    840
gccaccgggg agcccgaggc gtcctcgggc tcggggccgc cttccggggg cgcactgggg    900
cctcgggcgc tgttcgccag ccgcgtgcgc ccgggccagc gcgtgtacgt ggtggccgag    960
cgtgacgggg accgccggct cctgcccgcc gctgtgcaca gcgtgaccct aagcgaggag   1020
gccgcgggcg cctacgcgcc gctcacggcc cagggcacca ttctcatcaa ccgggtgctg   1080
gcctcgtgct acgcggtcat cgaggagcac agctgggcgc accgggcctt cgcgcccttc   1140
cgcctggcgc acgcgctcct ggctgcactg gcgcccgcgc gcacggaccg cggcggggac   1200
agcggcggcg gggaccgcgg gggcggcggc ggcagagtag ccctaaccgc tccaggtgct   1260
gccgacgctc cgggtgcggg ggccaccgcg ggcatccact ggtactcgca gctgctctac   1320
caaataggca cctggctcct ggacagcgag gccctgcacc cgctgggcat ggcggtcaag   1380
tccagcnnna gccggggggc cgggggaggg gcgcgggagg gggcc               1425

<210> SEQ ID NO 7
<211> LENGTH: 1622
<212> TYPE: DNA
<213> ORGANISM: Homo sapiens

<400> SEQUENCE: 7
catcagccca ccaggagacc tcgcccgccg ctcccccggg ctccccggcc atgtctcccg     60
cccggctccg gccccgactg cacttctgcc tggtcctgtt gctgctgctg gtggtgcccg    120
cggcatgggg ctgcgggccg ggtcgggtgg tgggcagccg ccggcgaccg ccacgcaaac    180
tcgtgccgct cgcctacaag cagttcagcc ccaatgtgcc cgagaagacc ctgggcgcca    240
```

-continued

| | |
|---|---|
| gcggacgcta tgaaggcaag atcgctcgca gctccgagcg cttcaaggag ctcaccccca | 300 |
| attacaatcc agacatcatc ttcaaggacg aggagaacac aggcgccgac cgcctcatga | 360 |
| cccagcgctg caaggaccgc ctgaactcgc tggctatctc ggtgatgaac cagtggcccg | 420 |
| gtgtgaagct gcgggtgacc gagggctggg acgaggacgc ccaccactca gaggagtccc | 480 |
| tgcattatga gggccgcgcg gtggacatca ccacatcaga ccgcgaccgc aataagtatg | 540 |
| gactgctggc gcgcttggca gtggaggccg gctttgactg ggtgtattac gagtcaaagg | 600 |
| cccacgtgca ttgctccgtc aagtccgagc actcggccgc agccaagacg ggcggctgct | 660 |
| tccctgccgg agcccaggta cgcctggaga gtggggcgcg tgtggccttg tcagccgtga | 720 |
| ggccgggaga ccgtgtgctg gccatggggg aggatgggag ccccaccttc agcgatgtgc | 780 |
| tcattttcct ggaccgcgag ccccacaggc tgagagcctt ccaggtcatc gagactcagg | 840 |
| accccccacg ccgcctggca ctcacacccg ctcacctgct ctttacggct gacaatcaca | 900 |
| cggagccggc agcccgcttc cgggccacat ttgccagcca cgtgcagcct ggccagtacg | 960 |
| tgctggtggc tggggtgcca ggcctgcagc ctgcccgcgt ggcagctgtc tctacacacg | 1020 |
| tggccctcgg ggcctacgcc ccgctcacaa agcatgggac actggtggtg gaggatgtgg | 1080 |
| tggcatcctg cttcgcggcc gtggctgacc accacctggc tcagttggcc ttctggcccc | 1140 |
| tgagactctt tcacagcttg gcatggggca gctggacccc gggggagggt gtgcattggt | 1200 |
| accccagct gctctaccgc ctgggcgtc tcctgctaga agagggcagc ttccacccac | 1260 |
| tgggcatgtc cggggcaggg agctgaaagg actccaccgc tgccctcctg gaactgctgt | 1320 |
| actgggtcca gaagcctctc agccaggagg gagctggccc tggaagggac ctgagctggg | 1380 |
| ggacactggc tcctgccatc tcctctgcca tgaagataca ccattgagac ttgactgggc | 1440 |
| aacaccagcg tcccccaccc gcgtcgtggt gtagtcatag agctgcaagc tgagctggcg | 1500 |
| aggggatggt tgttgacccc tctctcctag agaccttgag gctggcacgg cgactcccaa | 1560 |
| ctcagcctgc tctcactacg agttttcata ctctgcctcc cccattggga gggcccattc | 1620 |
| cc | 1622 |

<210> SEQ ID NO 8
<211> LENGTH: 1190
<212> TYPE: DNA
<213> ORGANISM: Homo sapiens

<400> SEQUENCE: 8

| | |
|---|---|
| atggctctcc tgaccaatct actgcccttg tgctgcttgg cacttctggc gctgccagcc | 60 |
| cagagctgcg gccgggccg ggggccggtt ggcggcgcc gctatgcgcg caagcagctc | 120 |
| gtgccgctac tctacaagca atttgtgccc ggcgtgccag agcggaccct gggcgccagt | 180 |
| gggccagcgg aggggagggt ggcaagggc tccgagcgct tccgggacct cgtgcccaac | 240 |
| tacaaccccg acatcatctt caaggatgag gagaacagtg gagccgaccg cctgatgacc | 300 |
| gagcgttgca aggagagggt gaacgctttg gccattgccg tgatgaacat gtggcccgga | 360 |
| gtgcgcctac gagtgactga gggctggac gaggacggcc accacgctca ggattcactc | 420 |
| cactacgaag gccgtgcttt ggacatcact acgtctgacc gcgaccgcaa caagtatggg | 480 |
| ttgctggcgc gcctcgcagt ggaagccggc ttcgactggg tctactacga gtcccgcaac | 540 |
| cacgtccacg tgtcggtcaa agctgataac tcactggcgg tccgggcggg cggctgcttt | 600 |
| ccgggaaatg caactgtgcg cctgtggagc ggcgagcgga aagggctgcg ggaactgcac | 660 |
| cgcggagact gggttttggc ggccgatgcg tcaggccggg tggtgcccac gccggtgctg | 720 |

```
ctcttcctgg accgggactt gcagcgccgg gcttcatttg tggctgtgga gaccgagtgg      780
cctccacgca aactgttgct cacgccctgg cacctggtgt ttgccgctcg agggccggcg      840
cccgcgccag cgactttgc accggtgttc gcgcgccggc tacgcgctgg ggactcggtg       900
ctggcgcccg gcggggatgc gcttcggcca gcgcgcgtgg cccgtgtggc gcggaggaa       960 gccgtgggcg tgttcgcgcc gctcaccgcg cacgggacgc tgctggtgaa cgatgtcctg     1020
gcctcttgct acgcggttct ggagagtcac cagtgggcgc accgcgcttt tgccccttg      1080 agactgctgc acgcgctagg ggcgctgctc cccggcgggg ccgtccagcc gactggcatg     1140
cattggtact ctcggctcct ctaccgctta gcggaggagc tactgggctg                1190

<210> SEQ ID NO 9
<211> LENGTH: 1416
<212> TYPE: DNA
<213> ORGANISM: Drosophila melanogaster

<400> SEQUENCE: 9
atggataacc acagctcagt gccttgggcc agtgccgcca gtgtcacctg tctctccctg      60
ggatgccaaa tgccacagtt ccagttccag ttccagctcc aaatccgcag cgagctccat     120
ctccgcaagc ccgcaagaag aacgcaaacg atgcgccaca ttgcgcatac gcagcgttgc     180
ctcagcaggc tgacctctct ggtggccctg ctgctgatcg tcttgccgat ggtctttagc     240
ccggctcaca gctgcggtcc tggccgagga ttgggtcgtc ataggcgcg caacctgtat      300 ccgctggtcc tcaagcagac aattcccaat ctatccgagt acacgaacag cgcctccgga     360
cctctggagg gtgtgatccg tcgggattcg cccaaattca aggacctcgt gcccaactac     420
aacagggaca tccttttccg tgacgaggaa ggcaccggag cggatggctt gatgagcaag     480
cgctgcaagg agaagctaaa cgtgctggcc tactcggtga tgaacgaatg gcccggcatc     540
cggctgctgg tcaccgagag ctgggacgag gactaccatc acggccagga gtcgctccac     600
tacgagggcc gagcggtgac cattgccacc tccgatcgcg accagtccaa atacggcatg     660
ctcgctcgcc tggccgtcga ggctggattc gattgggtct cctacgtcag caggcgccac     720
atctactgct ccgtcaagtc agattcgtcg atcagttccc acgtgcacgg ctgcttcacg     780
ccggagagca cagcgctgct ggagagtgga gtccggaagc cgctcggcga gctctctatc     840
ggagatcgtg ttttgagcat gaccgccaac ggacaggccg tctacagcga agtgatcctc     900
ttcatggacc gcaacctcga gcagatgcaa aactttgtgc agctgcacac ggacggtgga     960
gcagtgctca cggtgacgcc ggctcacctg gttagcgttt ggcagccgga gagccagaag    1020
ctcacgtttg tgtttgcgca tcgcatcgag gagaagaacc aggtgctcgt acgggatgtg    1080
gagacgggcg agctgaggcc ccagcgagtg gtcaagttgg gcagtgtgcg cagtaagggc    1140
gtggtcgcgc cgctgacccg cgagggcacc attgtggtca actcggtggc cgccagttgc    1200
tatgcggtga tcaacagtca gtcgctggcc cactgggac tggctcccat cgcctgctg     1260 tccacgctgg aggcgtggct gcccgccaag gagcagttgc acagttcgcc gaaggtggtg    1320
agctcggcgc agcagcagaa tggcatccat tggtatgcca atgcgctcta caaggtcaag    1380
gactacgtgc tgccgcagag ctggcgccac gattga                              1416

<210> SEQ ID NO 10
<211> LENGTH: 425
<212> TYPE: PRT
<213> ORGANISM: Gallus gallus
```

```
<400> SEQUENCE: 10

Met Val Glu Met Leu Leu Leu Thr Arg Ile Leu Leu Val Gly Phe Ile
1               5                   10                  15

Cys Ala Leu Leu Val Ser Ser Gly Leu Thr Cys Gly Pro Gly Arg Gly
            20                  25                  30

Ile Gly Lys Arg Arg His Pro Lys Lys Leu Thr Pro Leu Ala Tyr Lys
        35                  40                  45

Gln Phe Ile Pro Asn Val Ala Glu Lys Thr Leu Gly Ala Ser Gly Arg
    50                  55                  60

Tyr Glu Gly Lys Ile Thr Arg Asn Ser Glu Arg Phe Lys Glu Leu Thr
65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
            115                 120                 125

Glu Gly Trp Asp Glu Asp Gly His His Ser Glu Glu Ser Leu His Tyr
130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
            195                 200                 205

His Leu Glu His Gly Gly Thr Lys Leu Val Lys Asp Leu Ser Pro Gly
210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala
            260                 265                 270

His Leu Leu Phe Val Ala Pro Gln His Asn Gln Ser Glu Ala Thr Gly
            275                 280                 285

Ser Thr Ser Gly Gln Ala Leu Phe Ala Ser Asn Val Lys Pro Gly Gln
290                 295                 300

Arg Val Tyr Val Leu Gly Glu Gly Gly Gln Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350

Tyr Ala Val Ile Glu Glu His Ser Trp Ala His Trp Ala Phe Ala Pro
            355                 360                 365

Phe Arg Leu Ala Gln Gly Leu Leu Ala Leu Cys Pro Asp Gly Ala
370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415
```

```
Pro Leu Gly Met Val Ala Pro Ala Ser
            420                 425

<210> SEQ ID NO 11
<211> LENGTH: 396
<212> TYPE: PRT
<213> ORGANISM: Mus musculus

<400> SEQUENCE: 11

Met Ala Leu Pro Ala Ser Leu Leu Pro Leu Cys Cys Leu Ala Leu Leu
  1               5                  10                  15

Ala Leu Ser Ala Gln Ser Cys Gly Pro Gly Arg Gly Pro Val Gly Arg
             20                  25                  30

Arg Arg Tyr Val Arg Lys Gln Leu Val Pro Leu Leu Tyr Lys Gln Phe
         35                  40                  45

Val Pro Ser Met Pro Glu Arg Thr Leu Gly Ala Ser Gly Pro Ala Glu
     50                  55                  60

Gly Arg Val Thr Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                 85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
    290                 295                 300

Gly Asp Ala Leu Gln Pro Ala Arg Val Ala Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
```

```
                355                 360                 365
Leu Leu Pro Gly Gly Ala Val Gln Pro Thr Gly Met His Trp Tyr Ser
    370                 375                 380

Arg Leu Leu Tyr Arg Leu Ala Glu Glu Leu Met Gly
385                 390                 395

<210> SEQ ID NO 12
<211> LENGTH: 411
<212> TYPE: PRT
<213> ORGANISM: Mus musculus

<400> SEQUENCE: 12

Met Ser Pro Ala Trp Leu Arg Pro Arg Leu Arg Phe Cys Leu Phe Leu
1               5                   10                  15

Leu Leu Leu Leu Val Pro Ala Ala Arg Gly Cys Gly Pro Gly Arg
            20                  25                  30

Val Val Gly Ser Arg Arg Arg Pro Arg Lys Leu Val Pro Leu Ala
            35                  40                  45

Tyr Lys Gln Phe Ser Pro Asn Val Pro Glu Lys Thr Leu Gly Ala Ser
    50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Arg Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Lys Thr Gly Gly Cys Phe Pro Ala Gly Ala
        195                 200                 205

Gln Val Arg Leu Glu Asn Gly Glu Arg Val Ala Leu Ser Ala Val Lys
    210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
        275                 280                 285

His Phe Arg Ala Thr Phe Ala Ser His Val Gln Pro Gly Gln Tyr Val
    290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
                325                 330                 335
```

-continued

```
Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe Pro
        355                 360                 365

Ser Leu Ala Trp Gly Ser Trp Thr Pro Ser Glu Gly Val His Trp Tyr
    370                 375                 380

Pro Gln Met Leu Tyr Arg Leu Gly Arg Leu Leu Glu Ser Thr
385                 390                 395                 400

Phe His Pro Leu Gly Met Ser Gly Ala Gly Ser
                405                 410

<210> SEQ ID NO 13
<211> LENGTH: 437
<212> TYPE: PRT
<213> ORGANISM: Mus musculus

<400> SEQUENCE: 13

Met Leu Leu Leu Leu Ala Arg Cys Phe Leu Val Ile Leu Ala Ser Ser
1               5                  10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Arg Leu Arg Val Thr Glu Gly
        115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
        195                 200                 205

Glu Gln Gly Gly Thr Lys Leu Val Lys Asp Leu Arg Pro Gly Asp Arg
    210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
        275                 280                 285

Ala Leu Phe Ala Ser Arg Val Arg Pro Gly Gln Arg Val Tyr Val Val
    290                 295                 300
```

```
Ala Glu Arg Gly Gly Asp Arg Leu Leu Pro Ala Ala Val His Ser
305                 310                 315                 320

Val Thr Leu Arg Glu Glu Ala Gly Ala Tyr Ala Pro Leu Thr Ala
            325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
            355                 360                 365

Ala His Ala Leu Leu Ala Leu Ala Pro Ala Arg Thr Asp Gly Gly
        370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 14
<211> LENGTH: 418
<212> TYPE: PRT
<213> ORGANISM: Danio rerio

<400> SEQUENCE: 14

Met Arg Leu Leu Thr Arg Val Leu Leu Val Ser Leu Leu Thr Leu Ser
1               5                   10                  15

Leu Val Val Ser Gly Leu Ala Cys Gly Pro Gly Arg Gly Tyr Gly Arg
            20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Thr Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
    130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
```

-continued

```
                225                 230                 235                 240
Phe Thr Asp Arg Asp Ser Thr Thr Arg Arg Val Phe Tyr Val Ile Glu
                245                 250                 255
Thr Gln Glu Pro Val Glu Lys Ile Thr Leu Thr Ala Ala His Leu Leu
            260                 265                 270
Phe Val Leu Asp Asn Ser Thr Glu Asp Leu His Thr Met Thr Ala Ala
        275                 280                 285
Tyr Ala Ser Ser Val Arg Ala Gly Gln Lys Val Met Val Val Asp Asp
    290                 295                 300
Ser Gly Gln Leu Lys Ser Val Ile Val Gln Arg Ile Tyr Thr Glu Glu
305                 310                 315                 320
Gln Arg Gly Ser Phe Ala Pro Val Thr Ala His Gly Thr Ile Val Val
                325                 330                 335
Asp Arg Ile Leu Ala Ser Cys Tyr Ala Val Ile Glu Asp Gln Gly Leu
            340                 345                 350
Ala His Leu Ala Phe Ala Pro Ala Arg Leu Tyr Tyr Tyr Val Ser Ser
        355                 360                 365
Phe Leu Phe Pro Gln Asn Ser Ser Ser Arg Ser Asn Ala Thr Leu Gln
    370                 375                 380
Gln Glu Gly Val His Trp Tyr Ser Arg Leu Leu Tyr Gln Met Gly Thr
385                 390                 395                 400
Trp Leu Leu Asp Ser Asn Met Leu His Pro Leu Gly Met Ser Val Asn
                405                 410                 415
Ser Ser
```

<210> SEQ ID NO 15
<211> LENGTH: 462
<212> TYPE: PRT
<213> ORGANISM: Homo sapiens

<400> SEQUENCE: 15

```
Met Leu Leu Leu Ala Arg Cys Leu Leu Leu Val Leu Val Ser Ser Leu
1               5                   10                  15
Leu Val Cys Ser Gly Leu Ala Cys Gly Pro Gly Arg Gly Phe Gly Lys
                20                  25                  30
Arg Arg His Pro Lys Lys Leu Thr Pro Leu Ala Tyr Lys Gln Phe Ile
            35                  40                  45
Pro Asn Val Ala Glu Lys Thr Leu Gly Ala Ser Gly Arg Tyr Glu Gly
        50                  55                  60
Lys Ile Ser Arg Asn Ser Glu Arg Phe Lys Glu Leu Thr Pro Asn Tyr
65                  70                  75                  80
Asn Pro Asp Ile Ile Phe Lys Asp Glu Glu Asn Thr Gly Ala Asp Arg
                85                  90                  95
Leu Met Thr Gln Arg Cys Lys Asp Lys Leu Asn Ala Leu Ala Ile Ser
            100                 105                 110
Val Met Asn Gln Trp Pro Gly Val Lys Leu Arg Val Thr Glu Gly Trp
        115                 120                 125
Asp Glu Asp Gly His His Ser Glu Glu Ser Leu His Tyr Glu Gly Arg
    130                 135                 140
Ala Val Asp Ile Thr Thr Ser Asp Arg Asp Arg Ser Lys Tyr Gly Met
145                 150                 155                 160
Leu Ala Arg Leu Ala Val Glu Ala Gly Phe Asp Trp Val Tyr Tyr Glu
                165                 170                 175
Ser Lys Ala His Ile His Cys Ser Val Lys Ala Glu Asn Ser Val Ala
```

-continued

```
                180                 185                 190
Ala Lys Ser Gly Gly Cys Phe Pro Gly Ser Ala Thr Val His Leu Glu
            195                 200                 205
Gln Gly Gly Thr Lys Leu Val Lys Asp Leu Ser Pro Gly Asp Arg Val
        210                 215                 220
Leu Ala Ala Asp Asp Gln Gly Arg Leu Leu Tyr Ser Asp Phe Leu Thr
225                 230                 235                 240
Phe Leu Asp Arg Asp Asp Gly Ala Lys Lys Val Phe Tyr Val Ile Glu
                245                 250                 255
Thr Arg Glu Pro Arg Glu Arg Leu Leu Leu Thr Ala Ala His Leu Leu
            260                 265                 270
Phe Val Ala Pro His Asn Asp Ser Ala Thr Gly Glu Pro Glu Ala Ser
        275                 280                 285
Ser Gly Ser Gly Pro Pro Ser Gly Gly Ala Leu Gly Pro Arg Ala Leu
    290                 295                 300
Phe Ala Ser Arg Val Arg Pro Gly Gln Arg Val Tyr Val Val Ala Glu
305                 310                 315                 320
Arg Asp Gly Asp Arg Arg Leu Leu Pro Ala Ala Val His Ser Val Thr
                325                 330                 335
Leu Ser Glu Glu Ala Ala Gly Ala Tyr Ala Pro Leu Thr Ala Gln Gly
            340                 345                 350
Thr Ile Leu Ile Asn Arg Val Leu Ala Ser Cys Tyr Ala Val Ile Glu
        355                 360                 365
Glu His Ser Trp Ala His Arg Ala Phe Ala Pro Phe Arg Leu Ala His
    370                 375                 380
Ala Leu Leu Ala Ala Leu Ala Pro Ala Arg Thr Asp Arg Gly Gly Asp
385                 390                 395                 400
Ser Gly Gly Gly Asp Arg Gly Gly Gly Gly Arg Val Ala Leu Thr
                405                 410                 415
Ala Pro Gly Ala Ala Asp Ala Pro Gly Ala Gly Ala Thr Ala Gly Ile
            420                 425                 430
His Trp Tyr Ser Gln Leu Leu Tyr Gln Ile Gly Thr Trp Leu Leu Asp
        435                 440                 445
Ser Glu Ala Leu His Pro Leu Gly Met Ala Val Lys Ser Ser
    450                 455                 460

<210> SEQ ID NO 16
<211> LENGTH: 411
<212> TYPE: PRT
<213> ORGANISM: Homo sapiens

<400> SEQUENCE: 16

Met Ser Pro Ala Arg Leu Arg Pro Arg Leu His Phe Cys Leu Val Leu
1               5                   10                  15
Leu Leu Leu Val Val Pro Ala Ala Trp Gly Cys Gly Pro Gly Arg
            20                  25                  30
Val Val Gly Ser Arg Arg Arg Pro Pro Arg Lys Leu Val Pro Leu Ala
        35                  40                  45
Tyr Lys Gln Phe Ser Pro Asn Val Pro Glu Lys Thr Leu Gly Ala Ser
    50                  55                  60
Gly Arg Tyr Glu Gly Lys Ile Ala Arg Ser Ser Glu Arg Phe Lys Glu
65                  70                  75                  80
Leu Thr Pro Asn Tyr Asn Pro Asp Ile Ile Phe Lys Asp Glu Glu Asn
                85                  90                  95
```

```
Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
            115                 120                 125

Val Thr Glu Gly Trp Asp Glu Asp Gly His His Ser Glu Glu Ser Leu
        130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
225                 230                 235                 240

Ser Asp Val Leu Ile Leu Leu Asp Arg Glu Pro His Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Thr Ala Asp Asn His Thr Glu Pro Ala Ala
        275                 280                 285

Arg Phe Arg Ala Thr Phe Ala Ser His Val Gln Pro Gly Gln Tyr Val
    290                 295                 300

Leu Val Ala Gly Ala Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe His
        355                 360                 365

Ser Leu Ala Trp Gly Ser Trp Thr Pro Gly Glu Gly Val His Trp Tyr
    370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410

<210> SEQ ID NO 17
<211> LENGTH: 396
<212> TYPE: PRT
<213> ORGANISM: Homo sapiens

<400> SEQUENCE: 17

Met Ala Leu Leu Thr Asn Leu Leu Pro Leu Cys Cys Leu Ala Leu Leu
1               5                   10                  15

Ala Leu Pro Ala Gln Ser Cys Gly Pro Gly Arg Gly Pro Val Gly Arg
            20                  25                  30

Arg Arg Tyr Ala Arg Lys Gln Leu Val Pro Leu Leu Tyr Lys Gln Phe
        35                  40                  45

Val Pro Gly Val Pro Glu Arg Thr Leu Gly Ala Ser Gly Pro Ala Glu
    50                  55                  60
```

```
Gly Arg Val Ala Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                 85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Trp Ser Gly Glu Arg Lys Gly Leu Arg Glu Leu His Arg Gly Asp Trp
    210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Trp Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
    290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu His Ala Leu Gly Ala
        355                 360                 365

Leu Leu Pro Gly Gly Ala Val Gln Pro Thr Gly Met His Trp Tyr Ser
    370                 375                 380

Arg Leu Leu Tyr Arg Leu Ala Glu Glu Leu Leu Gly
385                 390                 395

<210> SEQ ID NO 18
<211> LENGTH: 471
<212> TYPE: PRT
<213> ORGANISM: Drosophila melanogaster

<400> SEQUENCE: 18

Met Asp Asn His Ser Ser Val Pro Trp Ala Ser Ala Ser Val Thr
 1               5                  10                  15

Cys Leu Ser Leu Asp Ala Lys Cys His Ser Ser Ser Ser Ser Ser
            20                  25                  30

Ser Lys Ser Ala Ala Ser Ser Ile Ser Ala Ile Pro Gln Glu Glu Thr
```

-continued

```
                35                  40                  45
Gln Thr Met Arg His Ile Ala His Thr Gln Arg Cys Leu Ser Arg Leu
 50                  55                  60
Thr Ser Leu Val Ala Leu Leu Leu Ile Val Leu Pro Met Val Phe Ser
 65                  70                  75                  80
Pro Ala His Ser Cys Gly Pro Gly Arg Gly Leu Gly Arg His Arg Ala
                 85                  90                  95
Arg Asn Leu Tyr Pro Leu Val Leu Lys Gln Thr Ile Pro Asn Leu Ser
                100                 105                 110
Glu Tyr Thr Asn Ser Ala Ser Gly Pro Leu Glu Gly Val Ile Arg Arg
                115                 120                 125
Asp Ser Pro Lys Phe Lys Asp Leu Val Pro Asn Tyr Asn Arg Asp Ile
130                 135                 140
Leu Phe Arg Asp Glu Glu Gly Thr Gly Ala Asp Arg Leu Met Ser Lys
145                 150                 155                 160
Arg Cys Lys Glu Lys Leu Asn Val Leu Ala Tyr Ser Val Met Asn Glu
                165                 170                 175
Trp Pro Gly Ile Arg Leu Leu Val Thr Glu Ser Trp Asp Glu Asp Tyr
                180                 185                 190
His His Gly Gln Glu Ser Leu His Tyr Glu Gly Arg Ala Val Thr Ile
                195                 200                 205
Ala Thr Ser Asp Arg Asp Gln Ser Lys Tyr Gly Met Leu Ala Arg Leu
                210                 215                 220
Ala Val Glu Ala Gly Phe Asp Trp Val Ser Tyr Val Ser Arg Arg His
225                 230                 235                 240
Ile Tyr Cys Ser Val Lys Ser Asp Ser Ser Ile Ser Ser His Val His
                245                 250                 255
Gly Cys Phe Thr Pro Glu Ser Thr Ala Leu Leu Glu Ser Gly Val Arg
                260                 265                 270
Lys Pro Leu Gly Glu Leu Ser Ile Gly Asp Arg Val Leu Ser Met Thr
                275                 280                 285
Ala Asn Gly Gln Ala Val Tyr Ser Glu Val Ile Leu Phe Met Asp Arg
                290                 295                 300
Asn Leu Glu Gln Met Gln Asn Phe Val Gln Leu His Thr Asp Gly Gly
305                 310                 315                 320
Ala Val Leu Thr Val Thr Pro Ala His Leu Val Ser Val Trp Gln Pro
                325                 330                 335
Glu Ser Gln Lys Leu Thr Phe Val Phe Ala Asp Arg Ile Glu Glu Lys
                340                 345                 350
Asn Gln Val Leu Val Arg Asp Val Glu Thr Gly Glu Leu Arg Pro Gln
                355                 360                 365
Arg Val Val Lys Val Gly Ser Val Arg Ser Lys Gly Val Val Ala Pro
                370                 375                 380
Leu Thr Arg Glu Gly Thr Ile Val Val Asn Ser Val Ala Ala Ser Cys
385                 390                 395                 400
Tyr Ala Val Ile Asn Ser Gln Ser Leu Ala His Trp Gly Leu Ala Pro
                405                 410                 415
Met Arg Leu Leu Ser Thr Leu Glu Ala Trp Leu Pro Ala Lys Glu Gln
                420                 425                 430
Leu His Ser Ser Pro Lys Val Val Ser Ala Gln Gln Asn Gly
                435                 440                 445
Ile His Trp Tyr Ala Asn Ala Leu Tyr Lys Val Lys Asp Tyr Val Leu
                450                 455                 460
```

Pro Gln Ser Trp Arg His Asp
465                 470

<210> SEQ ID NO 19
<211> LENGTH: 221
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(221)
<223> OTHER INFORMATION: Xaa=unknown amino acid

<400> SEQUENCE: 19

Cys Gly Pro Gly Arg Gly Xaa Gly Xaa Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Xaa Arg Asn Ser Glu
        35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Arg Cys Lys
65                  70                  75                  80

Asp Lys Leu Asn Xaa Leu Ala Ile Ser Val Met Asn Xaa Trp Pro Gly
                85                  90                  95

Val Xaa Leu Arg Val Thr Glu Gly Trp Asp Glu Asp Gly His His Xaa
            100                 105                 110

Glu Glu Ser Leu His Tyr Glu Gly Arg Ala Val Asp Ile Thr Thr Ser
        115                 120                 125

Asp Arg Asp Xaa Ser Lys Tyr Gly Xaa Leu Xaa Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
            180                 185                 190

Lys Asp Leu Xaa Pro Gly Asp Xaa Val Leu Ala Ala Asp Xaa Xaa Gly
        195                 200                 205

Xaa Leu Xaa Xaa Ser Asp Phe Xaa Xaa Phe Xaa Asp Arg
    210                 215                 220

<210> SEQ ID NO 20
<211> LENGTH: 174
<212> TYPE: PRT
<213> ORGANISM: Gallus gallus

<400> SEQUENCE: 20

Cys Gly Pro Gly Arg Gly Ile Gly Lys Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Thr Arg Asn Ser Glu
        35                  40                  45

Arg Phe Lys Glu Leu Thr Pro Asn Tyr Asn Pro Asp Ile Ile Phe Lys
    50                  55                  60

-continued

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125

Asp Arg Asp Arg Ser Lys Tyr Gly Met Leu Ala Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 21
<211> LENGTH: 176
<212> TYPE: PRT
<213> ORGANISM: Mus musculus

<400> SEQUENCE: 21

Cys Gly Pro Gly Arg Gly Pro Val Gly Arg Arg Arg Tyr Val Arg Lys
1               5                   10                  15

Gln Leu Val Pro Leu Leu Tyr Lys Gln Phe Val Pro Ser Met Pro Glu
            20                  25                  30

Arg Thr Leu Gly Ala Ser Gly Pro Ala Glu Gly Arg Val Thr Arg Gly
        35                  40                  45

Ser Glu Arg Phe Arg Asp Leu Val Pro Asn Tyr Asn Pro Asp Ile Ile
    50                  55                  60

Phe Lys Asp Glu Glu Asn Ser Gly Ala Asp Arg Leu Met Thr Glu Arg
65                  70                  75                  80

Cys Lys Glu Arg Val Asn Ala Leu Ala Ile Ala Val Met Asn Met Trp
                85                  90                  95

Pro Gly Val Arg Leu Arg Val Thr Glu Gly Trp Asp Glu Asp Gly His
            100                 105                 110

His Ala Gln Asp Ser Leu His Tyr Glu Gly Arg Ala Leu Asp Ile Thr
        115                 120                 125

Thr Ser Asp Arg Asp Arg Asn Lys Tyr Gly Leu Leu Ala Arg Leu Ala
    130                 135                 140

Val Glu Ala Gly Phe Asp Trp Val Tyr Tyr Glu Ser Arg Asn His Ile
145                 150                 155                 160

His Val Ser Val Lys Ala Asp Asn Ser Leu Ala Val Arg Ala Gly Gly
                165                 170                 175

<210> SEQ ID NO 22
<211> LENGTH: 175
<212> TYPE: PRT
<213> ORGANISM: Mus musculus

<400> SEQUENCE: 22

Cys Gly Pro Gly Arg Val Val Gly Ser Arg Arg Pro Pro Arg Lys
1               5                   10                  15

Leu Val Pro Leu Ala Tyr Lys Gln Phe Ser Pro Asn Val Pro Glu Lys
            20                  25                  30

Thr Leu Gly Ala Ser Gly Arg Tyr Glu Gly Lys Ile Ala Arg Ser Ser
        35                  40                  45

```
Glu Arg Phe Lys Glu Leu Thr Pro Asn Tyr Asn Pro Asp Ile Ile Phe
        50                  55                  60

Lys Asp Glu Glu Asn Thr Gly Ala Asp Arg Leu Met Thr Gln Arg Cys
 65                  70                  75                  80

Lys Asp Arg Leu Asn Ser Leu Ala Ile Ser Val Met Asn Gln Trp Pro
                 85                  90                  95

Gly Val Lys Leu Arg Val Thr Glu Gly Arg Asp Glu Asp Gly His His
                100                 105                 110

Ser Glu Glu Ser Leu His Tyr Glu Gly Arg Ala Val Asp Ile Thr Thr
                115                 120                 125

Ser Asp Arg Asp Arg Asn Lys Tyr Gly Leu Leu Ala Arg Leu Ala Val
        130                 135                 140

Glu Ala Gly Phe Asp Trp Val Tyr Tyr Glu Ser Lys Ala His Val His
145                 150                 155                 160

Cys Ser Val Lys Ser Glu His Ser Ala Ala Lys Thr Gly Gly
                165                 170                 175

<210> SEQ ID NO 23
<211> LENGTH: 174
<212> TYPE: PRT
<213> ORGANISM: Mus musculus

<400> SEQUENCE: 23

Cys Gly Pro Gly Arg Gly Phe Gly Lys Arg Arg His Pro Lys Lys Leu
1                5                  10                  15

Thr Pro Leu Ala Tyr Lys Gln Phe Ile Pro Asn Val Ala Glu Lys Thr
                20                  25                  30

Leu Gly Ala Ser Gly Arg Tyr Glu Gly Lys Ile Thr Arg Asn Ser Glu
            35                  40                  45

Arg Phe Lys Glu Leu Thr Pro Asn Tyr Asn Pro Asp Ile Ile Phe Lys
        50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Arg Leu Arg Val Thr Glu Gly Trp Asp Glu Asp Gly His His Ser
                100                 105                 110

Glu Glu Ser Leu His Tyr Glu Gly Arg Ala Val Asp Ile Thr Thr Ser
                115                 120                 125

Asp Arg Asp Arg Ser Lys Tyr Gly Met Leu Ala Arg Leu Ala Val Glu
        130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 24
<211> LENGTH: 174
<212> TYPE: PRT
<213> ORGANISM: Danio rerio

<400> SEQUENCE: 24

Cys Gly Pro Gly Arg Gly Tyr Gly Arg Arg His Pro Lys Lys Leu
1                5                  10                  15

Thr Pro Leu Ala Tyr Lys Gln Phe Ile Pro Asn Val Ala Glu Lys Thr
                20                  25                  30
```

Leu Gly Ala Ser Gly Arg Tyr Glu Gly Lys Ile Thr Arg Asn Ser Glu
            35                  40                  45

Arg Phe Lys Glu Leu Thr Pro Asn Tyr Asn Pro Asp Ile Ile Phe Lys
        50                  55                  60

Asp Glu Glu Asn Thr Gly Ala Asp Arg Leu Met Thr Gln Arg Cys Lys
65                  70                  75                  80

Asp Lys Leu Asn Ser Leu Ala Ile Ser Val Met Asn His Trp Pro Gly
                85                  90                  95

Val Lys Leu Arg Val Thr Glu Gly Trp Asp Glu Asp Gly His His Phe
            100                 105                 110

Glu Glu Ser Leu His Tyr Glu Gly Arg Ala Val Asp Ile Thr Thr Ser
        115                 120                 125

Asp Arg Asp Lys Ser Lys Tyr Gly Thr Leu Ser Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 25
<211> LENGTH: 174
<212> TYPE: PRT
<213> ORGANISM: Homo sapiens

<400> SEQUENCE: 25

Cys Gly Pro Gly Arg Gly Phe Gly Lys Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Ser Arg Asn Ser Glu
        35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125

Asp Arg Asp Arg Ser Lys Tyr Gly Met Leu Ala Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 26
<211> LENGTH: 175
<212> TYPE: PRT
<213> ORGANISM: Homo sapiens

<400> SEQUENCE: 26

Cys Gly Pro Gly Arg Val Val Gly Ser Arg Arg Arg Pro Pro Arg Lys
1               5                   10                  15

```
Leu Val Pro Leu Ala Tyr Lys Gln Phe Ser Pro Asn Val Pro Glu Lys
             20                  25                  30

Thr Leu Gly Ala Ser Gly Arg Tyr Glu Gly Lys Ile Ala Arg Ser Ser
         35                  40                  45

Glu Arg Phe Lys Glu Leu Thr Pro Asn Tyr Asn Pro Asp Ile Ile Phe
 50                  55                  60

Lys Asp Glu Glu Asn Thr Gly Ala Asp Arg Leu Met Thr Gln Arg Cys
 65                  70                  75                  80

Lys Asp Arg Leu Asn Ser Leu Ala Ile Ser Val Met Asn Gln Trp Pro
                 85                  90                  95

Gly Val Lys Leu Arg Val Thr Glu Gly Trp Asp Glu Asp Gly His His
             100                 105                 110

Ser Glu Ser Leu His Tyr Glu Gly Arg Ala Val Asp Ile Thr Thr
         115                 120                 125

Ser Asp Arg Asp Arg Asn Lys Tyr Gly Leu Leu Ala Arg Leu Ala Val
130                 135                 140

Glu Ala Gly Phe Asp Trp Val Tyr Tyr Glu Ser Lys Ala His Val His
145                 150                 155                 160

Cys Ser Val Lys Ser Glu His Ser Ala Ala Lys Thr Gly Gly
                165                 170                 175

<210> SEQ ID NO 27
<211> LENGTH: 176
<212> TYPE: PRT
<213> ORGANISM: Homo sapiens

<400> SEQUENCE: 27

Cys Gly Pro Gly Arg Gly Pro Val Gly Arg Arg Arg Tyr Ala Arg Lys
 1               5                  10                  15

Gln Leu Val Pro Leu Leu Tyr Lys Gln Phe Val Pro Gly Val Pro Glu
             20                  25                  30

Arg Thr Leu Gly Ala Ser Gly Pro Ala Glu Gly Arg Val Ala Arg Gly
         35                  40                  45

Ser Glu Arg Phe Arg Asp Leu Val Pro Asn Tyr Asn Pro Asp Ile Ile
 50                  55                  60

Phe Lys Asp Glu Glu Asn Ser Gly Ala Asp Arg Leu Met Thr Glu Arg
 65                  70                  75                  80

Cys Lys Glu Arg Val Asn Ala Leu Ala Ile Ala Val Met Asn Met Trp
                 85                  90                  95

Pro Gly Val Arg Leu Arg Val Thr Glu Gly Trp Asp Glu Asp Gly His
             100                 105                 110

His Ala Gln Asp Ser Leu His Tyr Glu Gly Arg Ala Leu Asp Ile Thr
         115                 120                 125

Thr Ser Asp Arg Asp Arg Asn Lys Tyr Gly Leu Leu Ala Arg Leu Ala
130                 135                 140

Val Glu Ala Gly Phe Asp Trp Val Tyr Tyr Glu Ser Arg Asn His Val
145                 150                 155                 160

His Val Ser Val Lys Ala Asp Asn Ser Leu Ala Val Arg Ala Gly Gly
                165                 170                 175
```